(12) United States Patent
Okamoto et al.

(10) Patent No.: US 9,018,238 B2
(45) Date of Patent: Apr. 28, 2015

(54) INHIBITOR OF CASEIN KINASE 1δ AND CASEIN KINASE 1ε

(75) Inventors: Masako Okamoto, Tokyo (JP); Kiyoshi Takayama, Sapporo (JP)

(73) Assignees: Pharmadesign, Inc., Tokyo (JP); NB Health Laboratory Co., Ltd., Sapporo-shi (JP)

( * ) Notice: Subject to any disclaimer, the term of this patent is extended or adjusted under 35 U.S.C. 154(b) by 404 days.

(21) Appl. No.: 13/201,309

(22) PCT Filed: Dec. 28, 2009

(86) PCT No.: PCT/JP2009/007329
§ 371 (c)(1),
(2), (4) Date: Aug. 12, 2011

(87) PCT Pub. No.: WO2010/092660
PCT Pub. Date: Aug. 19, 2010

(65) Prior Publication Data
US 2011/0294857 A1    Dec. 1, 2011

(30) Foreign Application Priority Data

Feb. 12, 2009 (JP) ................. 2009-030232
Mar. 19, 2009 (JP) ................. 2009-068390
Oct. 26, 2009 (JP) ................. 2009-245477

(51) Int. Cl.
| | | |
|---|---|---|
| A61K 31/422 | (2006.01) | |
| A61K 31/433 | (2006.01) | |
| A61K 31/4439 | (2006.01) | |
| C07D 413/06 | (2006.01) | |
| C07D 413/14 | (2006.01) | |
| C07D 417/14 | (2006.01) | |
| C07D 413/04 | (2006.01) | |
| C07D 263/18 | (2006.01) | |

(52) U.S. Cl.
CPC ............ C07D 413/04 (2013.01); C07D 263/18 (2013.01); A61K 31/422 (2013.01); A61K 31/433 (2013.01); A61K 31/4439 (2013.01); C07D 413/06 (2013.01); C07D 413/14 (2013.01); C07D 417/14 (2013.01)

(58) Field of Classification Search
CPC ............................ A61K 31/422; C07D 263/18
USPC ............................................. 514/376; 548/228
See application file for complete search history.

(56) References Cited

U.S. PATENT DOCUMENTS

2004/0180943 A1* 9/2004 Augelli-Szafran et al. ... 514/376
2007/0015768 A1* 1/2007 Alroy et al. ............. 514/255.03
2009/0176773 A1* 7/2009 Klussmann et al. ....... 514/230.5

FOREIGN PATENT DOCUMENTS

| JP | 2008-510704 A | 4/2008 |
|---|---|---|
| JP | 2008-510712 A | 4/2008 |
| WO | WO 2005007141 A2 * | 1/2005 |
| WO | 2006/023467 A1 | 3/2006 |
| WO | 2006/044626 A2 | 4/2006 |
| WO | WO 2006122546 A1 * | 11/2006 |

OTHER PUBLICATIONS http://www.cancer.gov/cancertopics/types/alphalist/y.*
Singh et. al., Progress in Neurobiology, 2007, Elsevier, vol. 81, pp. 29-44.*
Lindvall et. al., Nature, 2006, Nature Publishing Group, vol. 441, pp. 1094-1096.*
Beger et. al., World Journal of Surgery, 2003, Societe Internationale de Chirurgie, vol. 27, pp. 1075-1084.*
Chabner et. al., Nature Reviews Cancer, 2005, Nature Publishing Group, vol. 5, pp. 65-72.*
Leaf, Fortune, Mar. 9, 2004, Time Inc., pp. 1-13.*
Schwartzbaum et. al., Nature Clinical Practice Neurology, 2006, Nature Publishing Group, vol. 2, No. 9, pp. 494-503.*

(Continued)

*Primary Examiner* — Sarah Pihonak
(74) *Attorney, Agent, or Firm* — Westerman, Hattori, Daniels & Adrian, LLP

(57) ABSTRACT

There is provided an inhibitor that inhibits casein kinase 1δ and casein kinase 1ε, and thus, there is also provided a pharmaceutical agent useful for the treatment and/or prevention of a disease, with the pathological condition of which the mechanism of activation of casein kinase 1δ or casein kinase 1ε is associated. Particularly, the above-described inhibitor is used to provide a pharmaceutical agent useful for the treatment of circadian rhythm disorder (including sleep disorder), central neurodegenerative disease, and cancer.

An inhibitor of casein kinase 1δ and casein kinase 1ε, which comprises, as an active ingredient, an oxazolone derivative represented by the following general formula (1), a salt thereof, a solvate thereof, or a hydrate thereof:

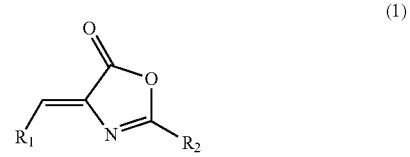

(1)

[wherein, in the formula (1), each of $R_1$ and $R_2$ independently represents any one of a substituted or unsubstituted 6-membered or 5-membered heterocyclic group optionally having a condensed ring, a substituted or unsubstituted aromatic hydrocarbon group optionally having a condensed ring, and a substituted or unsubstituted aromatic hydrocarbon lower alkyl group or aromatic hydrocarbon lower alkenyl group optionally having a condensed ring.]

20 Claims, No Drawings

(56) References Cited

OTHER PUBLICATIONS

Extended European Search Report dated Jun. 25, 2012, issued in corresponding European Patent Application No. 09839982.7.
European Office Action dated Feb. 8, 2013, issued in corresponding European Patent Application No. 09839982.7.
Worayuthakarn, R. et al., "Three Distinct Reactions of 3,4-Dihydroisoquinolines with Aziactotes: Novel Synthesis of Imidazoloisoquinolin-3-ones, Benzo[a]quinolizin-4-ones, and Benzo[d]azocin-4-ones", Organic Letters, vol. 8, No. 25, p. 5845-5848 (2006); cited in European Office Action dated Feb. 8, 2013.
2C47.txt pp. 1-609, May 15, 2006.
2CHL.txt, pp. 1-609, May 15, 2006.
2CMW.txt, pp. 1-609, May 15, 2006.
2IZR.txt, pp. 1-1582, Jul. 26, 2006.
2IZS.txt, pp. 1-470, Mar. 15, 2006.
2IZT.txt, pp. 1-470, Mar. 15, 2006.
2IZU.txt, pp. 1-505, Jul. 26, 2006.
Cozza, G. et al.; "Identification of novel protein kinase CK1 delta (CK1delta) inhibitors through structure-based virtual screening"; Bioorg Med Chem Lett., Oct. 15, 2008; 18(20): 5672-5675. Epub Aug. 26, 2008, pp. 1-17.
Xu, Y. et al.; "Modeling of a human circadian mutation yields novel insights into clock regulation by PER2"; NIH Public Access; Cell., Jan. 12, 2007, 128(1) pp. 59-70.
Knippschild, Uwe et al.; "The casein kinase 1 family; participation in multiple cellular processes in eukaryotes"; Cellular Signalling, No. 17, (2005), pp. 675-689.
Brockschmidt, C. et al.; "Anti-apoptotic and growth-stimulatory functions of CK1 delta and epsilon in ductal adenocarcinoma of the pancreas are inhibited by IC261 in vitro and vivo"; GUT Online, 2008, 57, pp. 799-806, originally published online Jan. 18, 2008.
Ko, Caroline H. et al.; "Molecular components of the mammalian ciradian clock"; Human Molecular Genetics 2006, vol. 15, Review Issue No. 2, pp. R271-R277.
Mashhoon, Neda et al.; "Crystal Structure of a Conformation-selective Casein Kinase-1 Inhibitor"; The Journal of Biological Chemistry; vol. 275, No. 26, Issue of Jun. 30, pp. 20052-20060, 2000.
Li, Guibin et al.; "Casein Kinase 1 Delta Phosphorylates Tau and Disrupts Its Binding to Microtubules"; The Journal of Biological Chemistry, vol. 279, No. 16, Issue of Apr. 16, pp. 15938-15945, 2004.
Hanger, Diane P. et al.; "Novel Phosphorylation Sites in Tau from Alzheimer Brain Support a Role for Casein Kinase 1 in Disease Pathogenesis"; The Journal of Biological Chemistry, vol. 282, No. 32, pp. 23645-23654, Aug. 10, 2007.
Badura, Lori et al.; "An Inhibitor of Casein Kinase epsilon Induces Phase Delays in Circadian Rhythms under Free-Running and Entrained Conditions"; The Journal of Pharmacology and Experimental Therapeutics; vol. 322, No. 2, pp. 730-738, 2007.
Ebisawa, Takashi; "Circadian Rhythms in the CNS and Peripheral Clock Disorders:Human Sleep Disorders and Clock Genes"; Journal of Pharmacological Sciences, vol. 103, pp. 150-154, (2007).
Longenecker, K.L et al., 1CKI. txt, pp. 1-532, Aug. 25, 1995.
Longenecker, K.L et al., 1CKJ.txt), pp. 1-380, Aug. 25, 1995.
Godl, Klaus et al.; "An efficient proteomics method to identify the cellular targets of protein kinase inhibitors"; Proc. National Academy of Sciences (PNAS), vol. 100, No. 26, Dec. 23, 2003, pp. 15434-15439.
Flajolet, Marc et al.; "Regulation of Alzheimer's disease amyloid-$\beta$ formation by casein kinase I"; Proc National Academy of Sciences (PNAS), vol. 104, No. 10, pp. 4159-4164, Mar. 6, 2007.
Rena, Graham; "D4476, a cell-permeant inhibitor of CK1, suppresses the site-specific phosphorylation and nuclear exclusion of FOXO1a"; European Molecular Biology Organization, EMBO reports, vol. 5, No. 1, 2004, pp. 60-65.
International Search Report of PCT/JP2009/007329, date of mailing Jan. 26, 2010.

* cited by examiner

INHIBITOR OF CASEIN KINASE 1δ AND CASEIN KINASE 1ε

TECHNICAL FIELD

The present invention relates to an inhibitor of casein kinase 1δ and casein kinase 1ε, which comprises, as an active ingredient, an oxazolone derivative, a salt thereof, a solvate thereof, or a hydrate thereof. The present invention relates to a pharmaceutical agent for treating diseases, with the pathological conditions of which the activation of casein kinase 1δ or casein kinase 1ε is associated. The present invention relates to a pharmaceutical agent comprising the inhibitor of casein kinase 1δ and casein kinase 1ε, which is useful for the treatment and/or prevention of, particularly, circadian rhythm disorder (including sleep disorder), central neurodegenerative disease, and cancer, among the diseases, with the pathological conditions of which the activation of casein kinase 1δ or casein kinase 1ε is associated.

BACKGROUND ART

Casein kinase 1 belongs to serine/threonine kinase (which phosphorylates a tyrosine residue in some cases). As its isoforms in mammals, seven types of isoforms, namely, α, β, γ1, γ2, γ3, δ, and ε, have been known. It has been known that these isoforms phosphorylate various types of different substrate proteins, and that the isoforms are able to activate, inactivate, stabilize or destabilize the functions of the proteins, and thus they are associated with regulation of the functions of various types of different organisms. Mammalian casein kinase 1δ or casein kinase 1ε has, as a structure thereof, a kinase domain that is similar to those of other isoforms. However, the N-terminal and C-terminal domains thereof are different from those of other isoforms. That is to say, the C-terminal domain has a plurality of autophosphorylation sites, and it is considered to be involved in regulation of autoenzyme activity. In addition, such a kinase domain comprises a sequence assumed to be associated with nuclear translocation (NLS: nuclear location signal) and a kinesin-like domain (KHD: kinesin homology domain).

It has been known that casein kinase 1δ and casein kinase 1ε are associated with circadian rhythm disorder, that casein kinase 1δ alone is associated with neurodegenerative disease, and that casein kinase 1δ and casein kinase 1ε are associated with cancer. Detailed information regarding the association of these casein kinases with the pathological conditions of the above-mentioned diseases has being known in studies regarding the interaction between the casein kinase 1δ and casein kinase 1ε, and target proteins interacting with the casein kinase 1δ and casein kinase 1ε, such as substrate proteins interacting with the corresponding casein kinase 1δ and casein kinase 1ε. Specific examples of a substrate protein phosphorylated by the casein kinase 1δ and casein kinase 1ε include a period protein (Per), a tau protein (tau), p53, and β-catenin.

Today, the core of the biological clock acting as a central generator of the circadian rhythm is considered to consist of approximately 10 types of gene interaction networks called "clock genes." Among these 5 types of gene groups, Per 1, 2 and 3 (Period 1, 2 and 3), Cry 1 and 2 (cryptochrome 1 and 2), Bmal1 (brain and muscle ARNT-like 1), and Clock (circadian locomotor output cycles kaput) encode transcription factors. On the other hand, CK1δ and 1ε encode casein kinase 1δ and casein kinase 1ε that phosphorylate these transcription factors. It has been known that the functional abnormality of these clock genes has influence on the circadian rhythm phenotypes of various types of animals including humans. Since the molecular mechanism of such a biological clock is well conserved beyond species, it is advantageous in that the studies of clock genes can be carried out in in vitro tests regarding the abnormality of the circadian rhythm phenotypes of humans. The Clock governs a pathway for generating activation signals, among biological clock interaction networks, and activates Per, Cry and other downstream target genes. On the other hand, Per and Cry, which govern a pathway for generating regulatory signals, act to suppress the activity of the Clock. Casein kinase 1δ and casein kinase 1ε phosphorylate Per and Cry, so as to promote the cytoplasmic degradation of Per. Moreover, the results of such phosphorylation are associated with the control of the nuclear translocation of these transcription factors and the stability thereof in the nucleus. Thus, it has been considered that the rhythm of internal molecular vibrations is governed in a living body. In the case of mammals, the biological clock is present in the suprachiasmatic nucleus (SCN), and this SCN biological clock operates together with the gene expression biological clocks of central and peripheral tissues, other than SCN.

Per has been known as a circadian rhythm regulatory protein in a living body. The mRNA and protein levels of Per vibrate in response to the circadian rhythm, and are closely associated with the control of the biological clock. For instance, it has been known that, with a decrease in the phosphorylation caused by casein kinase 1ε or casein kinase 1δ, a genetic disease having a human Per2 phosphorylation site mutation (S662G) progresses to familial advanced sleep phase syndrome (FASPS). This shows that Per plays an important role in sleep regulation. It has been known that a change in the intracellular protein amount of Per is controlled by the phosphorylation caused by casein kinase 1ε or casein kinase 1δ. That is, it has been known that, if Per is phosphorylated by these kinases, the stability of the protein significantly decreases.

Xu, Y. et al. have reported that human Per2 phosphorylation site mutated (S662G) transgenic mice were found to have the same phenotype as FASPS found in humans. Moreover, these researchers have studied the influence caused by a change in the expression level of casein kinase 1δ using hybrid mice between the above-described transgenic mice and casein kinase 1δ WT mice (WT: wild type) or casein kinase 1δ+/− (heterozygous knockout) mice. As a result, the researchers have reported that the above-described phenotype has been influenced thereby, and that the abnormality of the circadian rhythm phenotype found in the wild-type mice was corrected in the +/− mice. This report describes the phosphorylation status of Per2 and the importance of the association of casein kinase 1δ with the phosphorylation (Non Patent Literature 5). Furthermore, Badula, Loi et al. have reported that the phase of circadian rhythm can be significantly delayed by subcutaneously administering to rats a casein kinase 1ε inhibitory compound, 4-[3-cyclohexyl-5-(4-fluorophenyl)-3H-imidazol-4-yl]-pyrimidin-2-ylamine (PF-670462) (Non Patent Literature 4). Thus, the phosphorylation status of Per has a relationship with circadian rhythm, and the inhibitor of casein kinase 1δ or casein kinase 1ε provides a novel method of adjusting such circadian rhythm. It can be anticipated that a technique of shifting or resetting the phase of circadian rhythm contributes to the treatment of circadian rhythm disorder including various types of sleep disorders.

Almost no pharmaceutical agents for directly treating circadian rhythm disorder have been known in prior art techniques. In addition, as therapeutic agents for such sleep disorders, sleep inducing drugs have been developed and used in clinical sites. On the other hand, the development of drugs for improving circadian rhythm sleep disorder (shift work sleep disorder, jet lag syndrome, advanced sleep phase syndrome, and delayed sleep phase syndrome) and the like has not yet been completed. Also, drug therapy, which is based on the technique of shifting or resetting the phase of circadian rhythm for other sleep disorders (insomnia, sleep-related breathing disorder, central hypersomnia, parasomnia, and sleep-related movement disorder), has not yet been completed.

Hereinafter, the correlation of casein kinase 1δ or casein kinase 1ε with central neurodegenerative disease, and in particular, with Alzheimer's disease, will be described.

It has been well known that aggregation of a tau protein in an Alzheimer's disease lesion site is an important marker for the pathological conditions. Also, it has been well known that excessive phosphorylation of this tau protein is deeply associated with aggregation. A casein kinase 1 family that is excessively expressed in the lesion site is considered to include candidate kinases for phosphorylating the tau protein. Thus, among these casein kinases, Li, Guibon et al. have studied casein kinase 1δ using a HEK-293 cell expression line. As a result, they have demonstrated using a nonselective casein kinase 1 inhibitory compound, 3-[(2,3,6-trimethoxy phenyl)methylidenyl]-indolin-2-one (IC261), that casein kinase 1δ first associates with a tau protein in situ and the casein kinase 1δ directly phosphorylates the tau protein, and that the phosphorylated level in the site of the tau protein that is the same as that phosphorylated in vitro is increased due to the excessive expression of the casein kinase 1δ (Non Patent Literature 6). On the other hand, Hanger, Diane P. et al. have made a comparison by mass spectrometry between, what is called, insoluble tau (PHF-tau (paired helical filaments-tau), which is an extremely phosphorylated aggregate obtained from the lesion site of an Alzheimer's disease patient, and the phosphorylation site of a healthy human, and have then identified a phosphorylation site characteristic for the lesion site of the Alzheimer's disease patient. At the same time, based on the characteristics of the phosphorylation site, they suggested that, as candidate kinases, casein kinase 1δ, as well as glycogen synthase kinase 3β, is highly likely to be associated with the process of lesion development (Non Patent Literature 7).

Hereinafter, the correlation of casein kinase 1δ or casein kinase 1ε with central neurodegenerative disease, and particularly with Alzheimer's disease, will be further described.

With regard to Alzheimer's disease, it has been considered that accumulation of amyloid-β (Aβ) showing toxicity to nerve cells is associated with the lesion thereof. At the same time, it has been known that the expression of casein kinase 1 is increased in the lesion site of an Alzheimer's disease patient. It is considered that Aβ is formed by cleaving APP (amyloid precursor protein) with β-secretase (aspartyl protease β-secretase) and γ-secretase (presenin-dependent protease γ-secretase). Flajolet, Marc et al. have performed an in silico analysis to study a site commonly phosphorylated by casein kinases 1 that are assumed to be present in the sequences of the subunits of these APP, β-secretase and γ-secretase. Subsequently, based on the obtained results, they have attempted to excessively express casein kinase 1ε constitutively active to N2A cells (N2A-APP695 cells) that stably express APP. As a result, they have reported that the amounts of Aβ40 and Aβ42 had become approximately 2 times and 2.5 times higher than that of a control, respectively. Furthermore, they have also reported that, when a nonselective casein kinase 1 inhibitory compound IC261 was added to this system, the amounts of Aβ40 and Aβ42 were decreased, and further that the same results could be obtained also using other two different types of nonselective casein kinase 1 inhibitory compounds, CKI-7 and D4476 (Non Patent Literature 8).

These reports (Non Patent Literature 6, 7 and 8) strongly suggest that casein kinase 1, and particularly, casein kinase 1δ or casein kinase 1ε is associated with the development of Alzheimer's disease, and that Alzheimer's disease can be treated by inhibiting the activity of the above-described enzyme.

Moreover, the chromosome 21, in which an Alzheimer's disease-causing gene is assumed to be present, becomes trisomic (triploid) in the somatic cells of a Down's syndrome patient. Thus, it has been thought that Down's syndrome can be a model for the studies of the genetic background or development of Alzheimer's disease. In particular, abnormal accumulation of specific proteins, found in the two types of diseases, has been considered to be one important, pathological and biochemical indicator associated with the pathogenic mechanism thereof, and thus has been studied. As a matter of fact, it has been known that Down's syndrome patients often have Alzheimer's disease-like cerebral lesion after middle age (approximately 35 years old). These facts strongly suggest that, even regarding neurodegenerative disease associated with Down's syndrome, this disease can be treated by inhibiting the enzyme activity of casein kinase 1, and particularly, casein kinase 1δ or casein kinase 1ε.

In prior art techniques, there have been known almost no pharmaceutical agents for treating central neurodegenerative diseases including Alzheimer's disease, which involve, as a point of action, direct inhibition of the aggregation of a tau protein or amyloid β. In addition, in prior art techniques, drug therapy for impeding the progression of central neurodegenerative diseases based on the concerned mechanism has not yet been completed.

Hereinafter, the correlation of casein kinase 1δ or casein kinase 1ε with cancer, and particularly, with pancreatic cancer, will be described.

The casein kinase 1 family is associated with regulation of various important physiological activities in cells. The casein kinase 1 family phosphorylates a wide variety of substrate proteins. For example, a tumor suppressor factor p53 and an oncogene mdm2 are both important proteins for controlling canceration and, at the same time, are substrates of casein kinase 1. Depending on the phosphorylation status thereof, cell canceration is considered to be accelerated. Among isoforms of casein kinase 1, phosphorylation of p53 by casein kinase 1ε or casein kinase 1δ, a consequent change in the interaction between p53 and mdm2, and stabilization and activation of p53 have attracted a lot of attention. Furthermore, it has also been known that casein kinase 1ε or casein kinase 1δ is involved in a regulatory protein associated with the formation of a spindle as a central body during cell division, and that the casein kinase 1ε or casein kinase 1δ is involved in apoptosis mediated by TRAIL (tumor necrosis factor-related apoptosis inducing factor) and Fas.

By the way, pancreatic ductal adenocarcinomas (PDACs) have been considered to be refractory cancers. Brockschmidt, C. et al. have studied that casein kinase 1ε or casein kinase 1δ is highly expressed in PDACs. Based on the obtained results, a nonselective casein kinase 1 inhibitory compound IC261 was added to a human pancreatic cancer cell line in vitro. As a result, suppression of the cell growth was observed. At the same time, the same pancreatic cancer cell line was transplanted into the subcutis of a mouse, and the nonselective casein kinase 1 inhibitory compound IC261 was then administered to the mouse. As a result, Brockschmidt, C. et al. have reported that a significant effect of suppressing the growth of tumor cells was obtained as in the case of a gemcitabine administration group (Non Patent Literature 9).

In prior art techniques, a pharmaceutical agent that can be used as an anticancer agent based on inhibition of casein kinase 1ε or casein kinase 1δ has not been known in the prior art. Moreover, in prior art techniques, drug therapy for treating refractory pancreatic cancer based on the concerned mechanism has not yet been completed.

CITATION LIST

Patent Literature

[Patent Literature 1] JP Patent Publication (Kohyo) No. 2008-510712 A
[Patent Literature 2] JP Patent Publication (Kohyo) No. 2008-510704 A Non Patent Literature

[Non Patent Literature 1] Uwe Knippschild et al., Cellular Signaling, 17, 675-689 (2005)
[Non Patent Literature 2] Takashi Ebisawa, J. Pharmacol. Sci., 103, 150-154 (2007)
[Non Patent Literature 3] Caroline H. Ko et Jpseph S. Takahashi, Hu. Mol. Genetics, 15(2) R271-R277 (2006)
[Non Patent Literature 4] Lori Badura et al, J. Pharmacol. Exp. Therapy, 322, 730-738 (2007)
[Non Patent Literature 5] Xu, Y. et al., Cell 128, 59-70 (2007)
[Non Patent Literature 6] Li, Guibin et al., J. Biol. Chem., 279(16), 15938-15945 (2004)
[Non Patent Literature 7] Hanger, Diane P. et al., J. Biol. Chem., 282(32), 23645-23654 (2007)
[Non Patent Literature 8] Flajolet, Marc et al., Proc. Nat. Acad. Sci., 104(10), 4159-4164 (2007)
[Non Patent Literature 9] Brockschmidt, C. et al.: Gut, 57, 799-809 (2008)
[Non Patent Literature 10] Mashhoon, Neda et al., J. Biol. Chem., 275(26), 20052-20060 (2000)
[Non Patent Literature 11] Rena, Graham, et al., EMBO Rep., 5(1), 60-65, (2004)
[Non Patent Literature 12] Godl, Klaus, et al., Proc. Nat. Acad. Sci., 100(26), 15434-15439 (2003)
[Non Patent Literature 13] Cozza, Giorgio et al., Bioorg. Medicinal Chem. Lett., 18(20), 5622-5675 (2008)
[Non Patent Literature 14] Protein Data Bank [online], <URL: http://www.rcsb.org/pdb/>, ID No.: 2CMW (CK1gamma1), 2C47 (CK1gamma2), 2CHL, 2IZR, 2IZS, 2IZT, 2IZU (CK1gamma3), 1CKI, 1CKJ (CK1 delta)

DISCLOSURE OF INVENTION

Technical Problem

It is an object of the present invention to provide an inhibitor of casein kinase 1δ and casein kinase 1ε, which comprises, as an active ingredient, an oxazolone derivative, a salt thereof, a solvate thereof, or a hydrate thereof.

In addition, it is another object of the present invention to provide a pharmaceutical agent, which comprises the casein kinase 1δ and casein kinase 1ε selective inhibitor of the present invention as a pharmaceutically active ingredient, wherein the pharmaceutical agent is useful for the treatment and/or prevention of diseases, with the pathological conditions of which the activation of casein kinase 1δ or casein kinase 1ε is associated, whereby the functions of the casein kinase 1δ or casein kinase 1ε are regulated in vivo. Moreover, it is another object of the present invention to provide a pharmaceutical agent useful for the treatment and/or prevention of circadian rhythm disorder (including sleep disorder), central neurodegenerative disease and cancer, among the diseases, with the pathological conditions of which the activation of casein kinase 1δ or casein kinase 1ε is associated. Furthermore, it is another object of the present invention to provide a method for treating and/or preventing circadian rhythm disorder (including sleep disorder), central neurodegenerative disease and cancer, administering the above-described pharmaceutical agent to a subject.

Further, it is another object of the present invention to provide a novel oxazolone derivative, a pharmaceutically acceptable salt thereof, and a hydrate thereof.

Solution to Problem

To date, several compounds have been known as research reagents having casein kinase 1 inhibitory action, which are non-specific to casein kinase 1 isoforms. Representative examples of such a compound include IC261, D4476, and SB203580 (Non Patent Literature 10, 11 and 12). These compounds have not yet obtained properties sufficient to solve the problems. In the beginning, these compounds were anticipated to simply have casein kinase 1 selective inhibitory action, and they targeted casein kinase 1δ as an isoform. On the other hand, PF-670462 is a compound obtained as a result of requirements for achieving casein kinase 1ε selective inhibitory action. However, this compound also has inhibitory action on other kinases. It was incidentally found that this compound also has inhibitory action on casein kinase 1δ, and that the possession of this inhibitory action is pharmacologically significant (Non Patent Literature 4). Likewise, there have been known other compounds having such casein kinase 1ε selective inhibitory action, but their selective inhibition of isoforms is not clearly described (Patent Literatures 1 and 2). Moreover, it has been reported that a model was constructed on the basis of the information regarding the three-dimensional structure of a target protein, and that, what is called, virtual screening was then performed. However, the action of the obtained compound is just limited to inhibitory action on casein kinase 1δ (Non Patent Literature 13). That is to say, to date, nobody had focused on the fact that the possession of casein kinase 1 selective inhibitory action, and with regard to selective inhibition of its isoforms, the possession of casein kinase 1δ and casein kinase 1ε selective inhibitory action, are therapeutically significant, and nobody had conducted intensive studies directed towards discovering a compound of interest, as the present inventors have done.

In order to achieve the above-mentioned objects, for the purpose of discovering various types of compounds having inhibitory action on the phosphorylation ability of casein kinase 1δ and casein kinase 1ε, the present inventors have constructed a complex model on the bases of the information of the three-dimensional structures of other similar proteins including the casein kinase 1δ. Thereafter, the inventors have performed virtual screening using DOCK4 formed by introducing consensus score into the database of commercially available compounds (wherein the information of the three-dimensional structure of casein kinase 1δ had been registered in Protein Data Bank, and thus, it had already been known (Non Patent Literature 14)).

As a result, the present inventors have found that a compound represented by a general formula (1) as shown below has inhibitory action on the phosphorylation ability of casein kinase 1δ and casein kinase 1ε. Moreover, the inventors have found that the present compound has selective inhibitory action that has never been known so far. Thus, the inventors have clarified that this compound is useful as an active ingredient of a pharmaceutical agent for treating the above-described diseases. The present invention has been completed based on these findings.

Specifically, the present invention relates to an inhibitor of casein kinase 1δ and casein kinase 1ε, which comprises, as an active ingredient, an oxazolone derivative represented by the following general formula (1), a salt thereof, a solvate thereof, or a hydrate thereof:

[Formula 1]

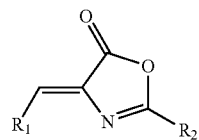

(1)

[wherein, in the formula (1), each of $R_1$ and $R_2$ independently represents any one of a substituted or unsubstituted 6-membered heterocyclic group optionally having a condensed ring, which is represented by the following formula (2):

[Formula 2]

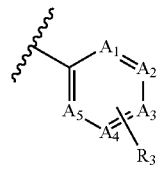

(2)

(wherein, in the formula (2), each of $A_1$ to $A_5$ independently represents a carbon atom or a nitrogen atom; and $R_3$ represents 1 to 5 identical or different substituents on $A_1$ to $A_5$, each of which independently represents a hydrogen atom, a halogen atom, a hydroxyl group, a nitro group, a cyano group, a carboxy group, a lower alkoxy group, a lower alkoxyalkyl group, a lower alkoxycarbonyl group, a lower acyl group, a lower acyloxy group, a lower acyloxyalkyl group, a carbamoyl group, a sulfamoyl group, a trifluoromethyl group, a substituted or unsubstituted allyl group, a substituted or unsubstituted heteroallyl group, a substituted or unsubstituted phenoxy group, a substituted or unsubstituted amino group, a substituted or unsubstituted lower alkyl group, a substituted or unsubstituted lower alkenyl group, a substituted or unsubstituted aromatic hydrocarbon group, or a substituted or unsubstituted aromatic heterocyclic group (wherein if there are a plurality of substituents, a ring may be formed by such a plurality of substituents)), a substituted or unsubstituted 5-membered heterocyclic group optionally having a condensed ring, which is represented by the following formula (3a) or (3b):

[Formula 3]

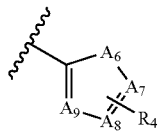

(3a)

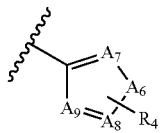

(3b)

(wherein, in the formula (3a) or (3b), $A_6$ represents an oxygen atom, a sulfur atom or a nitrogen atom; $A_7$, $A_8$ and $A_9$ each represent a carbon atom or a nitrogen atom; and $R_4$ represents 1 to 4 identical or different substituents on $A_6$ to $A_9$ (wherein $A_6$ represents a nitrogen atom), each of which independently represents a hydrogen atom, a halogen atom, a hydroxyl group, a nitro group, a cyano group, a carboxy group, a lower alkoxy group, a lower alkoxyalkyl group, a lower alkoxycarbonyl group, a lower acyl group, a lower acyloxy group, a lower acyloxyalkyl group, a carbamoyl group, a sulfamoyl group, a trifluoromethyl group, a substituted or unsubstituted allyl group, a substituted or unsubstituted heteroallyl group, a substituted or unsubstituted phenoxy group, a substituted or unsubstituted amino group, a substituted or unsubstituted lower alkyl group, a substituted or unsubstituted lower alkenyl group, a substituted or unsubstituted aromatic hydrocarbon group, or a substituted or unsubstituted aromatic heterocyclic group (wherein if there are a plurality of substituents, a ring may be formed by such a plurality of substituents)), a substituted or unsubstituted aromatic hydrocarbon group optionally having a condensed ring, which is represented by the following formula (4):

[Formula 4]

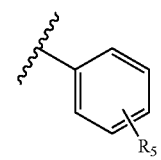

(4)

(wherein, in the formula (4), $R_5$ represents 1 to 5 identical or different substituents on a benzene ring, each of which independently represents a hydrogen atom, a halogen atom, a hydroxyl group, a nitro group, a cyano group, a carboxy group, a lower alkoxy group, a lower alkoxyalkyl group, a lower alkoxycarbonyl group, a lower acyl group, a lower acyloxy group, a lower acyloxyalkyl group, a carbamoyl group, a sulfamoyl group, a trifluoromethyl group, a substituted or unsubstituted allyl group, a substituted or unsubstituted heteroallyl group, a substituted or unsubstituted phenoxy group, a substituted or unsubstituted amino group, a substituted or unsubstituted lower alkyl group, a substituted or unsubstituted lower alkenyl group, a substituted or unsubstituted aromatic hydrocarbon group, or a substituted or unsubstituted aromatic heterocyclic group (wherein if there are a plurality of substituents, a ring may be formed by such a plurality of substituents)), and a substituted or unsubstituted aromatic hydrocarbon lower alkyl group or aromatic hydrocarbon lower alkenyl group optionally having a condensed ring, which is represented by the following formula (5):

[Formula 5]

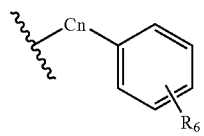

(5)

(wherein, in the formula (5), a lower alkyl portion or lower alkenyl portion represented by Cn (wherein n represents an integer of 1 to 10) may be any one of a linear portion, a branched portion, a cyclic portion and a combination thereof, containing 1 to 10 carbon atoms; and $R_6$ represents 1 to 5 identical or different substituents on a benzene ring, each of which independently represents a hydrogen atom, a halogen atom, a hydroxyl group, a nitro group, a cyano group, a carboxy group, a lower alkoxy group, a lower alkoxyalkyl group, a lower alkoxycarbonyl group, a lower acyl group, a lower acyloxy group, a lower acyloxyalkyl group, a carbamoyl group, a sulfamoyl group, a trifluoromethyl group, a substituted or unsubstituted allyl group, a substituted or unsubstituted heteroallyl group, a substituted or unsubstituted phenoxy group, a substituted or unsubstituted amino group, a substituted or unsubstituted lower alkyl group, a substituted or unsubstituted lower alkenyl group, a substituted or unsubstituted aromatic hydrocarbon group, or a substituted or unsubstituted aromatic heterocyclic group (wherein if there are a plurality of substituents, a ring may be formed by such a plurality of substituents))].

In addition, the present invention relates to a pharmaceutical agent useful for the treatment and/or prevention of diseases, with the process of development of the pathological conditions of which the activation of casein kinase 1δ or casein kinase 1ε is associated, wherein the inhibitor of casein kinase 1δ and casein kinase 1ε comprising, as an active ingredient, the oxazolone derivative represented by the above general formula (1), a salt thereof, a solvate thereof, or a hydrate thereof, is used. Moreover, the present invention relates to a pharmaceutical agent useful for the treatment and/or prevention of circadian rhythm disorder (including sleep disorder), central neurodegenerative disease and cancer, wherein the inhibitor of casein kinase 1δ and casein kinase 1ε comprising, as an active ingredient, the oxazolone derivative represented by the above general formula (1), a salt thereof, a solvate thereof, or a hydrate thereof, is used.

Furthermore, the present invention relates to a method for treating diseases, with the pathological conditions of which the mechanism of activation of casein kinase 1δ or casein kinase 1ε is associated, using the above-described pharmaceutical agent.

Further, the present invention relates to an oxazolone derivative represented by the following general formula (6), a pharmaceutically acceptable salt thereof, and a hydrate thereof:

[Formula 6]

(6)

[wherein, in the formula (6), $R_8$ represents a hydrogen atom or a methyl group; and $R_7$ represents any one of a substituted or unsubstituted 6-membered heterocyclic group optionally having a condensed ring, which is represented by the following formula (7):

[Formula 7]

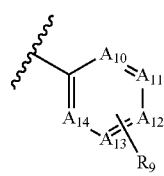

(7)

(wherein, in the formula (7), each of $A_{10}$ to $A_{14}$ independently represents a carbon atom or a nitrogen atom; and $R_9$ represents 1 to 5 identical or different substituents on $A_{10}$ to $A_{14}$, each of which independently represents a hydrogen atom, a halogen atom, a hydroxyl group, a nitro group, a cyano group, a carboxy group, a lower alkoxy group, a lower alkoxyalkyl group, a lower alkoxycarbonyl group, a lower acyl group, a lower acyloxy group, a lower acyloxyalkyl group, a carbamoyl group, a sulfamoyl group, a trifluoromethyl group, a substituted or unsubstituted allyl group, a substituted or unsubstituted heteroallyl group, a substituted or unsubstituted phenoxy group, a substituted or unsubstituted amino group, a substituted or unsubstituted lower alkyl group, a substituted or unsubstituted lower alkenyl group, a substituted or unsubstituted aromatic hydrocarbon group, or a substituted or unsubstituted aromatic heterocyclic group (wherein if there are a plurality of substituents, a ring may be formed by such a plurality of substituents)), and a substituted or unsubstituted 5-membered heterocyclic group optionally having a condensed ring, which is represented by the following formula (8a) or (8b):

[Formula 8]

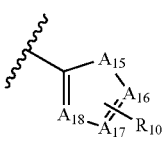

(8a)

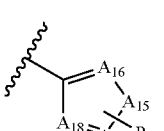

(8b)

(wherein, in the formula (8a) or (8b), $A_{15}$ represents an oxygen atom, a sulfur atom or a nitrogen atom; $A_{16}$, $A_{17}$ and $A_{18}$ each represent a carbon atom or a nitrogen atom; and $R_{10}$ represents 1 to 4 identical or different substituents on $A_{15}$ to $A_{18}$ (wherein $A_{15}$ represents a nitrogen atom), each of which independently represents a hydrogen atom, a halogen atom, a hydroxyl group, a nitro group, a cyano group, a carboxy group, a lower alkoxy group, a lower alkoxyalkyl group, a lower alkoxycarbonyl group, a lower acyl group, a lower acyloxy group, a lower acyloxyalkyl group, a carbamoyl group, a sulfamoyl group, a trifluoromethyl group, a substituted or unsubstituted allyl group, a substituted or unsubstituted heteroallyl group, a substituted or unsubstituted phenoxy group, a substituted or unsubstituted amino group, a substituted or unsubstituted lower alkyl group, a substituted or unsubstituted lower alkenyl group, a substituted or unsubstituted aromatic hydrocarbon group, or a substituted or unsubstituted aromatic heterocyclic group (wherein if there are a plurality of substituents, a ring may be formed by such a plurality of substituents))].

Advantageous Effects of Invention

The compound of the present invention can inhibit the activities of casein kinase 1δ and casein kinase 1ε. As a result, the present compound can treat diseases, with the pathological conditions of which the activation mechanism of the casein kinase 1δ or casein kinase 1ε is associated.

The compound of the present invention and the pharmaceutical agent of the present invention comprising the aforementioned compound as a pharmaceutically active ingredient can be used to treat diseases, with the pathological conditions of which the activation mechanism of the casein kinase 1δ or casein kinase 1ε is associated.

The compound of the present invention and the pharmaceutical agent of the present invention comprising the aforementioned compound as a pharmaceutically active ingredient have higher selectivity to the casein kinase 1δ and casein kinase 1ε than those of conventional compounds having casein kinase 1 inhibitory activity. As a result, the compound of the present invention and the pharmaceutical agent of the present invention comprising the aforementioned compound as a pharmaceutically active ingredient can be anticipated to have higher clinical efficiency than that of existing compounds, on diseases, with the pathological conditions the activation mechanism of casein kinase 1δ or casein kinase 1ε is associated. At the same time, the compound of the present invention and the pharmaceutical agent of the present invention comprising the aforementioned compound as a pharmaceutically active ingredient can be anticipated to have higher safety than that of existing compounds.

DESCRIPTION OF EMBODIMENTS

In the general formula (1), each of $R_1$ and $R_2$ independently represents any one of a substituted or unsubstituted 6-membered heterocyclic group optionally having a condensed ring, which is represented by the formula (2), a substituted or unsubstituted 5-membered heterocyclic group optionally having a condensed ring, which is represented by the formula (3a) or (3b), a substituted or unsubstituted aromatic hydrocarbon group optionally having a condensed ring, which is represented by the formula (4), and a substituted or unsubstituted aromatic hydrocarbon lower alkyl group or aromatic hydrocarbon lower alkenyl group optionally having a condensed ring, which is represented by the formula (5).

In addition, in the general formula (6), $R_7$ represents any one of a substituted or unsubstituted 6-membered heterocyclic group optionally having a condensed ring, which is represented by the formula (7), and a substituted or unsubstituted 5-membered heterocyclic group optionally having a condensed ring, which is represented by the formula (8a) or (8b). $R_8$ represents a hydrogen atom or a methyl group.

Herein, the term "heterocyclic ring" mainly indicates a 5-membered ring or a 6-membered ring, which contains one or more nitrogen atoms, oxygen atoms and sulfur atoms. Specific examples of the "6-membered heterocyclic ring" include, but are not limited to, a pyridine ring, a pyrazine ring, a pyrimidine ring, a pyridazine ring, a triazine ring, a pyridone ring, and a pyran ring. Specific examples of the "5-membered heterocyclic ring" include, but are not limited to, a pyrrole ring, a furan ring, a thiophene ring, an imidazole ring, an oxazole ring, a thiazole ring, pyrazole ring, an isoxazole ring, an isothiazole ring, a triazole ring, an oxadiazole ring, a thiadiazole ring, a tetrazole ring, an oxatriazole ring, and a thiatriazole ring.

The term "condensed heterocyclic ring" mainly indicates a 5-membered ring or a 6-membered ring, which contains one or more nitrogen atoms, oxygen atoms and sulfur atoms. It has a structure in which two or more rings share a side on one-on-one level. Specific examples of the "condensed heterocyclic ring" include, but are not limited to, an indole ring, a benzimidazole ring, a quinoline ring, a benzofuran ring, a chromene ring, a benzofuran ring, a benzodioxole ring, a dihydrobenzodioxin ring, and a dibenzofuran ring.

The "aromatic hydrocarbon" includes benzene naphthalene, anthracene, phenanthrene, and the like.

The "lower alkyl" may be any one of a saturated, linear portion, branched portion, cyclic portion and combination thereof, containing 1 to 20, and preferably 1 to 10 carbon atoms, whereas the "lower alkenyl" may be any one of an unsaturated, linear portion, branched portion, cyclic portion and combination thereof, containing 1 to 20, and preferably 1 to 10 carbon atoms. Thus, they are not particularly limited. Specific examples of a saturated linear alkyl group include methyl, ethyl, propyl, isopropyl, butyl, isobutyl, isopentyl, and neopentyl. Specific examples of a saturated cyclic alkyl group include cyclopropyl, cyclobutyl, cyclopentyl, and cyclohexyl. Specific examples of an unsaturated linear alkyl group include vinyl, propenyl, butenyl, and butedienyl. Specific examples of an unsaturated cyclic alkyl group include cyclopropenyl and cyclobutenyl.

In the formulae (2) to (5), (7) and (8), $R_3$ to $R_6$, $R_9$ and $R_{10}$ may be identical to or different from one another, and they independently represent a hydrogen atom, a halogen atom, a hydroxyl group, a nitro group, a cyano group, a carboxy group, a lower alkoxy group, a lower alkoxyalkyl group, a lower alkoxycarbonyl group, a lower acyl group, a lower acyloxy group, a lower acyloxyalkyl group, a carbamoyl group, a sulfamoyl group, a trifluoromethyl group, a substituted or unsubstituted allyl group, a substituted or unsubstituted heteroallyl group, a substituted or unsubstituted phenoxy group, a substituted or unsubstituted amino group, a substituted or unsubstituted lower alkyl group, a substituted or unsubstituted lower alkenyl group, a substituted or unsubstituted aromatic hydrocarbon group, or a substituted or unsubstituted aromatic heterocyclic group (wherein if there are a plurality of substituents, a ring may be formed by such a plurality of substituents). When the term "lower" is used with respect to an alkyl group and an alkenyl group or an alkyl portion and an alkenyl portion in the formula (5), it means that the aforementioned groups or portions each contain approximately 1 to 10, and preferably 1 to 4 carbon atoms, for example. When the term "halogen atom" is used in the present specification, it means any one of a fluorine atom, a chlorine atom, a bromine atom and an iodine atom. When the term "optionally having a substituent" is used to a certain functional group in the present specification, the number or position of such a substituent is not particularly limited.

The oxazolone derivatives represented by the general formula (1) and the general formula (6), which are contained as active ingredients in the inhibitor of casein kinase 1δ or casein kinase 1ε and the pharmaceutical agent according to the present invention, include their stereoisomers, such as tautomers, geometric isomers (for example, an E form, a Z form, etc.), and enantiomers, unless otherwise specified. That is to say, the oxazolone derivatives represented by the general formula (1) and the general formula (6) may have one or two or more asymmetric carbon atoms in some cases. These asymmetric carbon atoms may independently adopt either an (R) form or an (S) form as a stereochemical structure. The oxazolone derivative may be present in the form of a stereoisomer such as an enantiomer or a diastereoisomer. Any given stereoisomer having a pure form, any given mixture of stereoisomers, a racemic body, or the like can be used as an active ingredient of the pharmaceutical agent of the present invention.

The compound represented by the general formula (1) and a salt thereof are not limited. Examples include the following compounds and salts:

2-(4-bromo-3-methylphenyl)-4-(3-pyridinylmethylene)-5(4H)-oxazolone [or 2-(4-bromo-3-methylphenyl)-4-(pyridine-3-ylmethylene)oxazol-5(4H)-one] and an acceptable salt thereof;

2-(3-bromo-4-methoxyphenyl)-4-(3-pyridinylmethylene)-5(4H)-oxazolone and an acceptable salt thereof;

2-(2-phenylethenyl)-4-(3-pyridinylmethylene)-5(4H)-oxazolone and an acceptable salt thereof;

2-(5-methyl-2-thienyl)-4-(3-pyridinylmethylene)-5(4H)-oxazolone and an acceptable salt thereof;

4-((4-methoxyphenyl)methylene)-2-(2-thienyl)-5(4H)-oxazolone and an acceptable salt thereof;

Methyl 4-((5-oxo-2-(2-thienyl)oxazol-4(5H)-ylidene)methyl)benzoate and an acceptable salt thereof;

4-((4-methoxy-3-nitrophenyl)methylene)-2-(2-thienyl)-5(4H)-oxazolone and an acceptable salt thereof;

4-((6-chloro-1,3-benzodioxol-5-yl)methylene)-2-(2-thienyl)-5(4H)-oxazolone and an acceptable salt thereof;

4-((3-chloro-4-nitrophenyl)methylene)-2-(2-thienyl)-5(4H)-oxazolone and an acceptable salt thereof;

4-((3-bromo-4-nitrophenyl)methylene)-2-(2-thienyl)-5(4H)-oxazolone and an acceptable salt thereof;

4-((8-chloro-2,3-dihydro-1,4-benzodioxin-6-yl)methylene)-2-(2-thienyl)-5(4H)-oxazol one and an acceptable salt thereof; and 4-((1-methyl-1H-pyrazol-4-yl)methylene)-2-(2-thienyl)-5(4H)-oxazolone and an acceptable salt thereof.

All of the oxazolone derivatives of the present invention, which are represented by the general formula (1), can be obtained according to known publications or by applying ordinary chemical synthesis methods. These derivatives can be synthesized, for example, by the synthesis method described in U.S. Patent Laid-Open Publication No. 20040180943. Alternatively, with regard to the compounds described in paragraph [0026] above, commercially available products can be purchased from manufacturing companies such as Enamine, Pharmeks and Labotest.

The compound represented by the general formula (6), which is included in the compound represented by the general formula (1) (which is a compound in the subordinate concept of the compound represented by the general formula (1)), was newly synthesized in the present invention. Moreover, the fact that the compound represented by the general formula (6) has activity of inhibiting the activities of casein kinase 1δ and casein kinase 1ε has been disclosed by the present invention for the first time. As described in the "Examples" later, the novel oxazolone derivative of the present invention represented by the general formula (6) can be produced from a known starting substance according to an ordinary chemical synthesis method.

The compounds represented by the general formula (6) and salts thereof are not limited. Examples include the following compounds and salts:

4-((5-methoxy-3-pyridinyl)methylene)-2-(5-methyl-2-thienyl)-5(4H)-oxazolone and an acceptable salt thereof;

4-((5-methoxy-3-pyridinyl)methylene)-2-(2-thienyl)-5(4H)-oxazolone and an acceptable salt thereof;

4-((5-fluoro-3-pyridinyl)methylene)-2-(2-thienyl)-5(4H)-oxazolone and an acceptable salt thereof;

4-((2-fluoro-3-pyridinyl)methylene)-2-(2-thienyl)-5(4H)-oxazolone and an acceptable salt thereof;

4-((6-methoxy-3-pyridinyl)methylene)-2-(2-thienyl)-5(4H)-oxazolone and an acceptable salt thereof;

4-((6-acetylmethylamino-3-pyridinyl)methylene)-2-(2-thienyl)-5(4H)-oxazolone and an acceptable salt thereof;

4-((2-dimethylamino-3-pyridinyl)methylene)-2-(2-thienyl)-5(4H)-oxazolone and an acceptable salt thereof;

4-((6-methoxy-2-pyridinyl)methylene)-2-(2-thienyl)-5(4H)-oxazolone and an acceptable salt thereof;

4-((2-methoxy-4-pyridinyl)methylene)-2-(2-thienyl)-5(4H)-oxazolone and an acceptable salt thereof;

4-((1-methyl-1H-imidazol-4-yl)methylene)-2-(2-thienyl)-5(4H)-oxazolone and an acceptable salt thereof;

4-((5-acetyloxymethyl-2-furanyl)methylene)-2-(2-thienyl)-5(4H)-oxazolone and an acceptable salt thereof;

4-((5-methoxymethyl-2-furanyl)methylene)-2-(2-thienyl)-5(4H)-oxazolone and an acceptable salt thereof 4-((4-oxazoyl)methylene)-2-(2-thienyl)-5(4H)-oxazolone and an acceptable salt thereof 4-((1,2,3-thiadiazol-4-yl)methylene)-2-(2-thienyl)-5(4H)-oxazolone and an acceptable salt thereof 4-((1,5-dimethyl-1H-pyrazol-4-yl)methylene)-2-(2-thienyl)-5(4H)-oxazolone and an acceptable salt thereof 4-((1,3-dimethyl-1H-pyrazol-4-yl)methylene)-2-(2-thienyl)-5(4H)-oxazolone and an acceptable salt thereof 4-((2,6-dimethoxy-3-pyridinyl)methylene)-2-(2-thienyl)-5(4H)-oxazolone and an acceptable salt thereof;

4-((6-methoxy-2-methyl-3-pyridinyl)methylene)-2-(2-thienyl)-5(4H)-oxazolone and an acceptable salt thereof; and 4-((2-chloro-6-methoxy-3-pyridinyl)methylene)-2-(2-thienyl)-5(4H)-oxazolone and an acceptable salt thereof.

The present invention has been completed on the basis of the fact that the present inventors have found for the first time that the compounds of the present invention represented by the general formula (1) and the general formula (6) inhibit the activities of casein kinase 1δ and casein kinase 1ε, and that the inventors have produced the novel oxazolone derivative represented by the general formula (6).

According to a preferred embodiment of the present invention, there is provided an inhibitor compound that inhibits casein kinase 1δ and casein kinase 1ε, wherein the compound comprises, as an active ingredient, a substituted pyridine derivative represented by the general formula (1) or the general formula (6), a salt thereof, a solvate thereof, or a hydrate thereof. Moreover, according to another preferred embodiment of the present invention, there is provided a pharmaceutical agent for treating diseases, with the pathological conditions of which the activation of casein kinase 1δ or casein kinase 1ε is associated, and particularly, circadian rhythm disorder (including sleep disorder), central neurodegenerative disease and cancer, wherein the pharmaceutical agent comprises, as a pharmacologically active ingredient, the above-described compound.

The casein kinase 1δ in the present invention may be called with similar names or alias names, such as "Casein Kinase 1 delta," "Casein kinase 1 isoform delta," "CK1(-) delta," "CK1d", "HCKID," "Casein Kinase 1δ," "casein kinase 1 isoform δ," and "CK1(-)δ." In the present invention, casein kinase 1δ means a protein comprising an amino acid sequence that is identical to or substantially identical to the amino acid sequences registered under registration Nos. NP_001884.2, NP_620693.1, NP_620690.1 and NP_082150.1 in the database of NCBI Reference Sequences (RefSeq) published by the National Center for Biotechnology Information (NCBI).

Herein, the "protein comprising an amino acid sequence that is substantially identical to . . . " means a protein, which comprises an amino acid sequence having identity of approximately 60% or more, preferably approximately 70% or more, more preferably approximately 80%, 81%, 82%, 83%, 84%, 85%, 86%, 87%, 88%, 89%, 90%, 91%, 92%, 93%, 94%, 95%, 96%, 97% or 98%, and most preferably approximately 99%, at the amino acid sequence level with the above-described amino acid sequences having RefSeq Nos. NP_001884.2, NP_620693.1, NP_620690.1 and NP_082150.1, and which has the activity of protein phosphorylation enzyme.

Otherwise, the protein comprising an amino acid sequence substantially identical to the amino acid sequences having RefSeq Nos. NP_001884.2, NP_620693.1, NP_620690.1, NP_082150.1 is a protein, which consists of an amino acid sequence comprising a deletion, substitution or addition of one or several (preferably about 1 to 30, more preferably about 1 to 10, and further preferably 1 to 5) amino acids with respect to the amino acid sequences having RefSeq Nos. NP_001884.2, NP_620693.1, NP_620690.1 and NP_082150.1, and which the activity of protein phosphorylation enzyme.

The casein kinase 1ε in the present invention may be called with similar names or alias names, such as "Casein Kinase 1 epsilon," "Casein kinase 1 isoform epsilon," "CK1(-) epsilon," "CK1e", "HCKIE," "Casein Kinase 1ε," "casein kinase 1 isoform ε," and "CK1(-)ε." In the present invention, casein kinase 1ε means a protein comprising an amino acid sequence that is identical to or substantially identical to the amino acid sequences registered under registration Nos. NP_001885.1, NP_689407.1 and NP_038795.3 in the database of NCBI Reference Sequences (RefSeq) published by the National Center for Biotechnology Information (NCBI).

Herein, the "protein comprising an amino acid sequence that is substantially identical to . . . " means a protein, which comprises an amino acid sequence having identity of approximately 60% or more, preferably approximately 70% or more, more preferably approximately 80%, 81%, 82%, 83%, 84%, 85%, 86%, 87%, 88%, 89%, 90%, 91%, 92%, 93%, 94%, 95%, 96%, 97% or 98%, and most preferably approximately 99%, at the amino acid sequence level with the above-described amino acid sequences having RefSeq Nos. NP_001885.1, NP_689407.1 and NP_038795.3, and which has the activity of protein phosphorylation enzyme.

Otherwise, the protein comprising an amino acid sequence substantially identical to the amino acid sequences having RefSeq Nos. NP_001885.1, NP_689407.1 and NP_038795.3 is a protein, which consists of an amino acid sequence comprising a deletion, substitution or addition of one or several (preferably about 1 to 30, more preferably about 1 to 10, and further preferably 1 to 5) amino acids with respect to the amino acid sequences having RefSeq Nos. NP_001885.1, NP_689407.1 and NP_038795.3, and which the activity of protein phosphorylation enzyme.

The diseases, with the pathological conditions of which the activation mechanism of casein kinase 1δ or casein kinase 1ε is associated, are not limited. Examples of such diseases include circadian rhythm disorder (including sleep disorder), neurodegenerative disease, and cancer.

In the present specification, the type of circadian rhythm disorder is not limited. The circadian rhythm disorder includes mood disorder and sleep disorder. Such sleep disorder is circadian rhythm sleep disorder, and the circadian rhythm sleep disorder includes a disease selected from the group consisting of shift work sleep disorder, jet lag syndrome, advanced sleep phase syndrome, and delayed sleep phase syndrome. Moreover, the sleep disorder includes a disease selected from the group consisting of insomnia, sleep-related breathing disorder, central hypersomnia, parasomnia, and sleep-related movement disorder. Furthermore, the above-described mood disorder is selected from either depressive disorder or bipolar disorder, and the depressive disorder is major depressive disorder. Further, the mood disorder is selected from either depressive disorder or bipolar disorder, and the bipolar disorder is selected from the group consisting of bipolar type-I disorder or bipolar type-II disorder. Still further, examples of the disease in the present invention include insomnia, sleep-related breathing disorder, central hypersomnia, circadian rhythm sleep disorder, parasomnia, sleep-related movement disorder, and sleep disorder caused by other reasons.

In the present specification, insomnia includes psychophysiologic insomnia caused by stress or the like, insomnia caused by medical disease, and the like. Sleep-related breathing disorder includes central sleep apnea syndrome, obstructive sleep apnea syndrome, sleep-related hypoventilation/anoxemia syndrome, and the like. Central hypersomnia includes narcolepsy, idiopathic hypersomnia, recurrent hypersomnia, and the like. Circadian rhythm sleep disorder includes shift work sleep disorder, jet lag syndrome, advanced sleep phase syndrome, delayed sleep phase syndrome, and the like. Parasomnia includes sleep walking, REM sleep behavior disorder, and the like. Sleep-related movement disorder includes restless legs syndrome, periodic limb movement disorder, and the like.

In the present specification, the type of neurodegenerative disease is not limited. Examples of central neurodegenerative disease include: neurodegenerative disease caused by Alzheimer's disease, Parkinson's disease or Down's syndrome; nerve degeneration caused by physical nerve damage (brain tissue damage such as brain contusion, and nerve damage caused by head injury and the like); and nerve degeneration caused by nerve damage occurred after ischemia or ischemic reperfusion include: stroke, cerebral infarction, cerebral hemorrhage, cerebral ischemia, subarachnoid hemorrhage, aneurysmal hemorrhage, myocardial infarction, hypoxia, anoxia and nerve damage caused by grand mal/cerebral ischemia.

The type of cancer that arises from the pancreas is not limited in the present specification. Examples of such cancer include pancreatic duct cancer, invasive pancreatic duct cancer, pancreatic endocrine tumor, intraductal papillary mucinous tumor, mucinous cystoma, acinar cell cancer, and metastatic pancreatic cancer.

As active ingredients of the pharmaceutical agent of the present invention, in addition to the compounds represented by the above general formula (1) and general formula (6), physiologically acceptable salts thereof may also be used. When an acidic group is present, examples of the salts that can be formed therewith include: the salts of alkaline metals and alkaline-earth metals such as lithium, sodium, potassium, magnesium and calcium; the salts of amines such as ammonia, methylamine, dimethylamine, trimethylamine, dicyclohexylamine, tris(hydroxymethyl)aminomethane, N,N-bis(hydroxyethyl)piperazine, 2-amino-2-methyl-1-propanol, ethanolamine, N-methyl glucamine and L-glucamine; and salts formed with basic amino acids such as lysine, δ-hydroxylysine and arginine. When a basic group is present, examples of the salts that can be formed therewith include: salts with mineral acids such as hydrochloric acid, hydrobromic acid, sulfuric acid, nitric acid and phosphoric acid; salts with organic acids such as methanesulfonic acid, benzenesulfonic acid, paratoluenesulfonic acid, acetic acid, propionic acid, tartaric acid, fumaric acid, maleic acid, malic acid, oxalic acid, succinic acid, citric acid, benzoic acid, mandelic acid, cinnamic acid, lactic acid, glycolic acid, glucuronic acid, ascorbic acid, nicotinic acid and salicylic acid; and salts with acidic amino acids such as aspartic acid and glutamic acid.

Furthermore, as active ingredients of the pharmaceutical agent of the present invention, the solvates or hydrates of the compounds represented by the above general formula (1) and general formula (6) or the salts thereof may also be used.

With regard to the pharmaceutical agent of the present invention, the compounds represented by the above general formula (1) and general formula (6), the pharmacologically acceptable salts thereof, the solvates thereof or the hydrates thereof, which are contained as active ingredients, may be directly administered. In general, however, it is desired to administer the pharmaceutical agent of the present invention in the form of a pharmaceutical composition comprising the above-mentioned substance as an active ingredient and one or two or more pharmaceutical additives. As an active ingredient of the pharmaceutical agent of the present invention, two or more types of the above-mentioned substances may be used in combination. It is also possible to mix into the above-described pharmaceutical composition, the active ingredients of other pharmaceutical agents for treating and/or preventing diseases with the pathological conditions of which the activation mechanism of casein kinase 1δ or casein kinase 1ε is associated. It is also possible to mix into the above-described pharmaceutical composition, the active ingredients of other pharmaceutical agents for treating and/or preventing circadian rhythm disorder (including sleep disorder), central neurodegenerative disease and cancer, among the aforementioned diseases.

The type of a pharmaceutical composition is not particularly limited. Examples of a dosage form include a tablet, a capsule, a granule, a powder, a syrup, a suspending agent, a suppository, an ointment, a cream agent, a gel agent, a patch, an inhalant, and an injection. These pharmaceutical agents are prepared in accordance with ordinary methods. It is to be noted that a liquid agent may adopt a dosage form in which the agent is dissolved or suspended in water or a suitable solvent when used. In addition, a tablet or a granule may be coated according to well known methods. In the case of an injection, it is prepared by dissolving the compound of the present invention in water. The compound of the present invention may also be dissolved in a normal saline or a glucose solution, as necessary. Otherwise, a buffer or a preservative may also be added to the present compound. The pharmaceutical agent of the present invention is provided in the form of any given pharmaceutical agent for use in oral administration or parenteral administration. For example, it can be prepared in the form of: pharmaceutical compositions for oral administration, such as a granule, a fine grain agent, a powder, a hard capsule, a soft capsule, a syrup, an emulsion, a suspending agent or a liquid agent; and pharmaceutical compositions for parenteral administration, such as an injection for intravenous administration, intramuscular administration or subcutaneous administration, a drop, a transdermal agent, a transmucosal agent, a nasal drop, an inhalant, or a suppository. An injection, a drop or the like may be prepared in the dosage form of freeze-dried powders, and the powders may be then dissolved in a suitable aqueous medium such as a normal saline when used. Moreover, it is also possible that a sustained release agent coated with macromolecules and the like is directly administered into the brain.

The types of pharmaceutical additives used in the production of the pharmaceutical composition, the ratio of such pharmaceutical additives to the active ingredient, or a method for producing a pharmaceutical composition can be appropriately selected by a person skilled in the art, depending on the form of the composition. As pharmaceutical additives, inorganic or organic substances, or solid or liquid substances can be used. In general, such pharmaceutical additives can be mixed in a weight percentage amount from 1% to 90% with respect to the weight of the active ingredient. Specific examples of such a substance include lactose, glucose, mannit, dextrin, cyclodextrin, starch, sucrose, magnesium aluminometasilicate, synthetic aluminum silicate, carboxymethylcellulose sodium, hydroxypropyl starch, carboxymethylcellulose calcium, ion exchange resin, methyl cellulose, gelatin, gum arabic, hydroxypropyl cellulose, hydroxypropylmethyl cellulose, polyvinylpyrrolidone, polyvinyl alcohol, light anhydrous silicic acid, magnesium stearate, talc, Tragacanth, bentonite, veegum, titanium oxide, sorbitan fatty acid ester, sodium lauryl sulfate, glycerin, fatty acid glycerin ester, purified lanolin, glycerinated gelatin, polysorbate, macrogol, vegetable oil, wax, liquid paraffin, white petrolatum, fluorocarbon, nonionic surfactant, propylene glycol, and water.

In order to produce a solid agent for oral administration, an active ingredient is mixed with an excipient such as lactose, starch, crystalline cellulose, calcium lactate or silicic acid anhydride to form a powder agent. Otherwise, if necessary, a binder such as saccharose, hydroxypropyl cellulose or polyvinylpyrrolidone, a disintegrator such as carboxymethyl cellulose or carobxymethylcellulose calcium, and other additives are further added to the mixture, and the obtained mixture is then subjected to a dry or wet granulating method, so as to form a granule agent. Moreover, in order to produce a tablet, such a powder agent or a granule agent may be subjected to direct tableting, or a lubricant such as magnesium stearate or talc may be added to the powder agent or granule agent and the obtained mixture may be then subjected to tableting. Such a granule agent or a tablet may be coated with an enteric coating base such as hydroxypropylmethyl cellulose phthalate or a methacrylic acid-methyl methacrylate polymer, so as to prepare an enteric-coated agent. Alternatively, such a granule agent or a tablet may also be coated with ethyl cellulose, carnauba wax, hydrogenated oil or the like, so as to prepare a sustained release agent. Furthermore, in order to produce a capsule, a powder agent or a granule agent is filled into a hard capsule. Otherwise, the active ingredient is directly coated with a gelatin film, or it is dissolved in glycerin, polyethylene glycol, sesame oil, olive oil or the like and is then coated with a gelatin film, so as to prepare a soft capsule.

In order to produce an injection, the active ingredient, and as necessary, a pH adjuster such as hydrochloric acid, sodium hydroxide, lactose, lactic acid, sodium, sodium monohydrogen phosphate or sodium dihydrogen phosphate, an isotonizing agent such as sodium chloride or glucose, and other additives, are dissolved in distilled water for injection, and the obtained solution is then subjected to aseptic filtration and is then filled into an ampule. Otherwise, mannitol, dextrin, cyclodextrin, gelatin and the like are added to the obtained solution, followed by vacuum-freeze drying, so as to prepare an injection that is to be dissolved when used. Moreover, lecithin, polysorbate 80, polyoxyethylene hydrogenated castor oil or the like is added to the active ingredient to emulsify it in water, so as to prepare an emulsion for injection.

In order to produce an agent for rectal administration, the active ingredient, together with a suppository base material such as cacao butter, fatty acid tri-, di- and mono-glycerides, or polyethlene glycol, is dissolved by humidification, and the obtained solution is then poured into a mold, followed by cooling. Otherwise, the active ingredient is dissolved in polyethylene glycol, soybean oil or the like, and the obtained solution is then coated with a gelatin film.

In order to produce an external agent for skin, the active ingredient is added to white petrolatum, beeswax, liquid paraffin, polyethylene glycol or the like, and the mixture is humidified if necessary, and it is then kneaded, so as to prepare an ointment. Otherwise, the active ingredient is kneaded together with an adhesive such as rosin or an alkyl acrylate polymer, and the obtained mixture is then expanded on a non-woven fabric such as polyalkyl, so as to prepare a tape agent.

The applied dose and number of doses of the pharmaceutical agent of the present invention are not particularly limited. The applied dose and the number of doses can be selected, as appropriate, by a doctor's decision, depending on various conditions such as the purpose of prevention and/or treatment of deterioration and progression of a target disease, the type of the disease, the body weight, age and other conditions of a patient, etc. In general, the applied dose is approximately 0.01 to 1000 mg (the weight of the active ingredient) per adult per day via oral administration. Such a dose can be administered once or divided over several administrations per day, or every several days. When the pharmaceutical agent of the present invention is used as an injection, it is desired that a dose of 0.01 to 100 mg (the weight of the active ingredient) is administered per adult per day continuously or intermittently.

Using a carrier capable of preventing the immediate elimination of an agent from the inside of a body, the pharmaceutical agent of the present invention can be prepared in the form of a sustained release agent such as an implanted tablet or a delivery system encapsulated into a microcapsule. For example, there can be used biodegradable biocompatible polymers such as ethylene vinyl acetate, polyacid anhydride, polyglycolic acid, collagen, polyorthoester, and polylacetic acid. Such materials can be easily prepared by a person skilled in the art. In addition, a liposome suspension can also be used as a pharmaceutically acceptable carrier. The type of an available liposome is not limited. The liposome can be prepared as a lipid composition containing phosphatidyl choline, cholesterol and a PEG derivative of phosphatidylethanol (PEG-PE) to a size suitable for use, by passing it through a filter with an appropriate pore size, and it is then purified by a reverse-phase evaporation method.

The pharmaceutical agent of the present invention can be prepared as a pharmaceutical composition, and it can be included in a vessel or pack, together with an administration manual, so as to prepare a kit. When the pharmaceutical composition according to the present invention is provided as a kit, different constituents contained in the pharmaceutical composition are wrapped with different vessels, and they are then mixed immediately before use. Thus, the constituents are individually wrapped because it enables long-term storage without losing the functions of active constituents.

A reagent contained in the kit is supplied into a certain type of vessel, in which constituents maintain their activity for a long period of time and they are not adsorbed on the material of the vessel and are not degraded. For instance, a sealed glass ampule contains a buffer that has been wrapped under neutral non-reactive gas such as nitrogen gas. The ampule is made of glass, an organic polymer such as polycarbonate or polystyrene, ceramic, metal, other suitable materials that are commonly used to retain the reagent, and the like. Examples of other suitable vessels include a simple bottle produced from similar substances for ampule, and a wrapping material, the inside of which is lined with aluminum or alloy foil. Other vessels include a test tube, a vial, a flask, a bottle, a syringe, and a similar product thereof. The vessel has an aseptic access port, such as a bottle having a stopper that is penetrable with a subcutaneous injection needle.

In addition, an instruction manual is attached to the kit. The instruction manual for the kit consisting of the present pharmaceutical composition is printed on a paper or other materials, and/or it may be supplied as an electrically or electromagnetically readable medium, such as a floppy (registered trademark) disk, CD-ROM, DVD-ROM, a Zip disk, a video tape, or an audio tape. A detailed instruction manual may be actually attached into the kit, or it may be published on a website which is designated by a kit manufacturer or distributer and is then noticed via an electric mail.

Moreover, the present invention provides a method for treating a disease administering the pharmaceutical agent of the present invention to a subject.

The therapeutic method of the present invention includes a method for treating a disease that is developed as a result of the association of the activation mechanism of casein kinase 1δ or casein kinase 1ε with the pathological condition thereof, or the disease of an affected mammal.

Herein, the term "treatment" is used to mean that the progression and deterioration of the pathological conditions of a disease are inhibited or alleviated in a mammal that has been affected with or is suspected to have the disease, and thereby, the term "treatment" is used to mean a therapeutic means directed towards inhibiting or alleviating the progression and deterioration of various symptoms of the disease.

Moreover, the term "disease" means diseases as a whole, with the pathological conditions of which the activation mechanism of casein kinase 1δ or casein kinase 1ε is associated. Thus, the type of the disease is not particularly limited. Examples of such a disease include insomnia, sleep-related breathing disorder, central hypersomnia, circadian rhythm sleep disorder, parasomnia, and sleep-related movement disorder. The sleep disorder of the circadian rhythm sleep disorder is circadian rhythm sleep disorder, and the circadian rhythm sleep disorder includes shift work sleep disorder, jet lag syndrome, advanced sleep phase syndrome, and delayed sleep phase syndrome. The mood disorder of the circadian rhythm disorder includes depressive disorder and bipolar disorder. In addition, the concerned disease also includes: neurodegenerative disease caused by Alzheimer's disease, Parkinson's disease or Down's syndrome; central neurodegenerative disease caused by cerebrovascular disorder; cancer as a whole, the type of which is not specified; and particularly, cancer derived from the pancreas, such as pancreatic duct cancer, invasive pancreatic duct cancer, pancreatic endocrine tumor, intraductal papillary mucinous tumor, mucinous cystoma, acinar cell cancer, and metastatic pancreatic cancer.

The "mammal" as a subject in need of a treatment means any given animal classified into Mammalia, and the type of the mammal is not particularly limited. Examples of such a mammal include humans, pet animals such as a dog, a cat or a rabbit, and livestock animals such as a bovine, a swine, a sheep or a horse. A particularly preferred "mammal" is a human.

Next, the present invention will be described in specific examples. However, these examples are not intended to limit the scope of the present invention.

Example 1

4-((5-Methoxy-3-pyridinyl)methylene)-2-(5-methyl-2-thienyl)-5(4H)-oxazolone

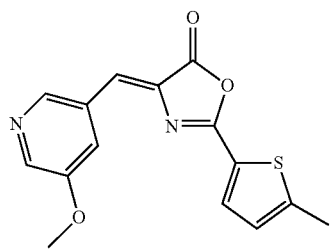 [SMILES: COc1cncc(/C=C2\N=C(c3ccc(C)s3)OC2=O)c1]

[Formula 9]

To a screw-capped test tube, N-[(5-methyl-2-thienyl)carbonyl]glycine (60 mg, 0.3 mmol), 5-methoxy-3-pyridinecarboxaldehyde (45 mg, 0.3 mmol), sodium acetate (25 mg, 0.3 mmol) and acetic anhydride (0.3 mL) were added. The test tube was sealed, and it was then stirred at an external temperature of 90° C. Three hours later, the temperature of the reaction solution was returned to room temperature, and water (1.5 mL) was then added thereto. The obtained mixture was stirred at the same temperature as described above for 1.5 hours. Thereafter, the precipitated crystal was collected by filtration, and it was washed with water (5 mL) and was then dried under reduced pressure, so as to obtain 51 mg of the above-captioned compound.

$^1$H-NMR (400 MHz, DMSO-$d_6$, δ).

8.83 (s, 1H), 8.36 (s, 1H), 8.31 (s, 1H), 7.84 (d, J=3.7 Hz, 1H), 7.28 (s, 1H), 7.09 (d, J=3.7 Hz, 1H), 3.91 (s, 3H), 2.60 (s, 3H).

ESI-MS m/z 301 (M+H)$^+$.

Example 2

4-((5-Methoxy-3-pyridinyl)methylene)-2-(2-thienyl)-5(4H)-oxazolone

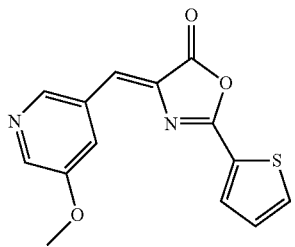 [SMILES: COc1cncc(/C=C2\N=C(c3cccs3)OC2=O)c1]

[Formula 10]

To a screw-capped test tube, N-(2-thienylcarbonyl)glycine (56 mg, 0.3 mmol), 5-methoxy-3-pyridinecarboxaldehyde (45 mg, 0.3 mmol), sodium acetate (25 mg, 0.3 mmol) and acetic anhydride (0.3 mL) were added. The test tube was sealed, and it was then stirred at an external temperature of 90° C. Three hours later, the temperature of the reaction solution was returned to room temperature, and water (1.5 mL) was then added thereto. The obtained mixture was stirred at the same temperature as described above for 1.5 hours. Thereafter, the precipitated crystal was collected by filtration, and it was washed with water (5 mL) and was then dried under reduced pressure, so as to obtain 40 mg of the above-captioned compound.

$^1$H-NMR (400 MHz, DMSO-$d_6$, δ).

8.86 (s, 1H), 8.38 (s, 1H), 8.32 (s, 1H), 8.16 (d, J=4.9 Hz, 1H), 8.02 (d, J=3.8 Hz, 1H), 7.37 (dd, J=4.8, 3.9 Hz, 1H), 7.34 (s, 1H), 3.92 (s, 3H).

ESI-MS m/z 287 (M+H)$^+$.

Example 3

4-((5-Fluoro-3-pyridinyl)methylene)-2-(2-thienyl)-5(4H)-oxazolone

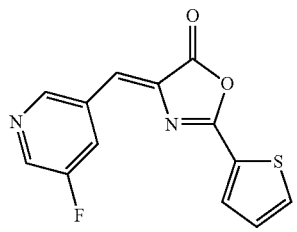 [SMILES: O=C1OC(c2cccs2)=N/C1=C\c1cncc(F)c1]

[Formula 11]

To a screw-capped test tube, N-(2-thienylcarbonyl)glycine (56 mg, 0.3 mmol), 5-fluoro-3-pyridinecarboxaldehyde (41 mg, 0.3 mmol), sodium acetate (25 mg, 0.3 mmol) and acetic anhydride (0.3 mL) were added. The test tube was sealed, and it was then stirred at an external temperature of 90° C. Three hours later, the temperature of the reaction solution was returned to room temperature, and water (1.5 mL) was then added thereto. The obtained mixture was stirred at the same temperature as described above for 1.5 hours. Thereafter, the precipitated crystal was collected by filtration, and it was washed with water (5 mL) and was then dried under reduced pressure, so as to obtain 56 mg of the above-captioned compound.

$^1$H-NMR (400 MHz, DMSO-$d_6$, δ).

9.13 (s, 1H), 8.67 (s, 1H), 8.53 (s, 1H), 8.20 (d, J=4.8 Hz, 1H), 8.06 (d, J=3.8 Hz, 1H), 7.37 (dd, J=4.8, 3.8 Hz, 1H), 7.33 (s, 1H).

ESI-MS m/z 275 (M+H)$^+$.

Example 4

4-((2-Fluoro-3-pyridinyl)methylene)-2-(2-thienyl)-5(4H)-oxazolone

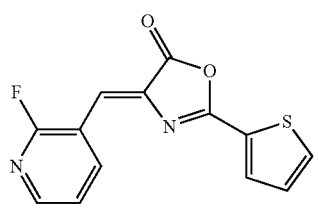 [SMILES: O=C1OC(c2cccs2)=N/C1=C\c1cccnc1F]
[Formula 12]

To a screw-capped test tube, N-(2-thienylcarbonyl)glycine (56 mg, 0.3 mmol), 2-fluoropyridin-3-carboxaldehyde (41 mg, 0.3 mmol), sodium acetate (25 mg, 0.3 mmol) and acetic anhydride (0.3 mL) were added. The test tube was sealed, and it was then stirred at an external temperature of 90° C. Three hours later, the temperature of the reaction solution was returned to room temperature, and water (1.5 mL) was then added thereto. The obtained mixture was stirred at the same temperature as described above for 1.5 hours. Thereafter, the precipitated crystal was collected by filtration, and it was washed with water (5 mL) and was then dried under reduced pressure, so as to obtain 53 mg of the above-captioned compound.

$^1$H-NMR (400 MHz, DMSO-d$_6$, δ).
9.09 (t, J=8.0 Hz, 1H), 8.34 (d, J=8.0 Hz, 1H), 8.20 (d, J=4.9 Hz, 1H), 8.06 (d, J=3.7 Hz, 1H), 7.60 (d, J=8.0 Hz, 1H), 7.39 (dd, J=4.8, 3.7 Hz, 1H), 7.10 (s, 1H).

Example 5

4-((6-Methoxy-3-pyridinyl)methylene)-2-(2-thienyl)-5(4H)-oxazolone

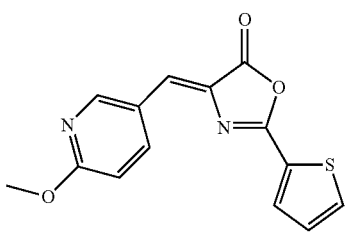 [SMILES: COc1ccc(/C=C2\N=C(c3cccs3)OC2=O)cn1]
[Formula 13]

To a screw-capped test tube, N-(2-thienylcarbonyl)glycine (56 mg, 0.3 mmol), 6-methoxy-3-pyridinecarboxaldehyde (45 mg, 0.3 mmol), sodium acetate (25 mg, 0.3 mmol) and acetic anhydride (0.3 mL) were added. The test tube was sealed, and it was then stirred at an external temperature of 90° C. Three hours later, the temperature of the reaction solution was returned to room temperature, and water (1.5 mL) was then added thereto. The obtained mixture was stirred at the same temperature as described above for 1.5 hours. Thereafter, the precipitated crystal was collected by filtration, and it was washed with water (5 mL) and was then dried under reduced pressure, so as to obtain 56 mg of the above-captioned compound.

$^1$H-NMR (400 MHz, DMSO-d$_6$, δ).
8.87 (s, 1H), 8.69 (d, J=8.8 Hz, 1H), 8.12 (d, J=4.8 Hz, 1H), 7.98 (d, J=3.8 Hz, 1H), 7.34 (dd, J=4.8, 3.8 Hz, 1H), 7.04 (d, J=8.8 Hz, 1H), 3.94 (s, 3H).
ESI-MS m/z 287 (M+H)$^+$.

Example 6

4-((6-Acetylmethylamino-3-pyridinyl)methylene)-2-(2-thienyl)-5(4H)-oxazolone

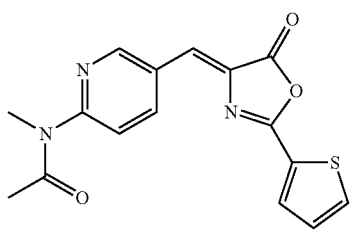
[Formula 14]

To a screw-capped test tube, N-(2-thienylcarbonyl)glycine (56 mg, 0.3 mmol), 6-(methylamino)-3-pyridinecarboxaldehyde (45 mg, 0.3 mmol), sodium acetate (25 mg, 0.3 mmol) and acetic anhydride (0.3 mL) were added. The test tube was sealed, and it was then stirred at an external temperature of 90° C. Three hours later, the temperature of the reaction solution was returned to room temperature, and water (1.5 mL) was then added thereto. The obtained mixture was stirred at the same temperature as described above for 1.5 hours. Thereafter, the precipitated crystal was collected by filtration, and it was washed with water (5 mL) and was then dried under reduced pressure, so as to obtain 28 mg of the above-captioned compound.

$^1$H-NMR (400 MHz, DMSO-d$_6$, δ).
9.10 (s, 1H), 8.71 (d, J=8.8 Hz, 1H), 8.16 (d, J=3.8 Hz, 1H), 8.02 (d, J=3.8 Hz, 1H), 7.78 (d, J=8.8 Hz, 1H), 7.36 (s, 1H), 3.38 (s, 3H), 2.20 (s, 3H).
ESI-MS m/z 328 (M+H)$^+$.

Example 7

4-((2-Dimethylamino-3-pyridinyl)methylene)-2-(2-thienyl)-5(4H)-oxazolone

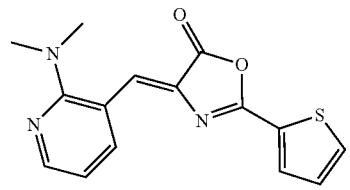
[Formula 15]

To a screw-capped test tube, N-(2-thienylcarbonyl)glycine (56 mg, 0.3 mmol), 2-(dimethylamino)-3-pyridinecarboxaldehyde (50 mg, 0.3 mmol), sodium acetate (25 mg, 0.3 mmol) and acetic anhydride (0.3 mL) were added. The test tube was sealed, and it was then stirred at an external temperature of 90° C. Three hours later, the temperature of the reaction solution was returned to room temperature, and water (1.5 mL) was then added thereto. The obtained mixture was stirred at the same temperature as described above for 1.5 hours. Thereafter, the precipitated crystal was collected by filtration, and it was washed with water (5 mL) and was then dried under reduced pressure, so as to obtain 29 mg of the above-captioned compound.

$^1$H-NMR (400 MHz, DMSO-d$_6$, δ).

8.64 (d, J=7.7 Hz, 1H), 8.26 (d, J=4.6 Hz, 1H), 8.12 (d, J=4.8 Hz, 1H), 7.96 (d, J=3.8 Hz, 1H), 7.35 (dd, J=3.8, 4.8 Hz, 1H), 7.15 (s, 1H), 7.04 (dd, J=4.7, 7.7 Hz), 2.97 (s, 6H).

ESI-MS m/z 300 (M+H)$^+$.

Example 8

4-((6-Methoxy-2-pyridinyl)methylene)-2-(2-thienyl)-5(4H)-oxazolone

[Formula 16]

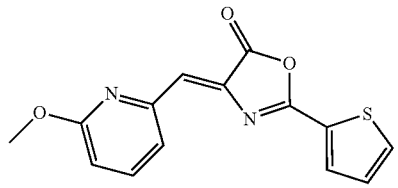 [SMILES: COc1cc(/C=C2\N=C(c3cccs3)OC2=O)ccn1]

To a screw-capped test tube, N-(2-thienylcarbonyl)glycine (56 mg, 0.3 mmol), 6-methoxy-2-pyridinecarboxaldehyde (46 mg, 0.3 mmol), sodium acetate (25 mg, 0.3 mmol) and acetic anhydride (0.3 mL) were added. The test tube was sealed, and it was then stirred at an external temperature of 90° C. Three hours later, the temperature of the reaction solution was returned to room temperature, and water (1.5 mL) was then added thereto. The obtained mixture was stirred at the same temperature as described above for 1.5 hours. Thereafter, the precipitated crystal was collected by filtration, and it was washed with water (5 mL) and was then dried under reduced pressure, so as to obtain 38 mg of the above-captioned compound.

$^1$H-NMR (400 MHz, DMSO-d$_6$, δ).

8.25 (d, J=7.1 Hz, 1H), 8.18 (d, J=4.9 Hz, 1H), 8.03 (d, J=3.8 Hz, 1H), 7.91 (d, J=7.9 Hz, 1H), 7.38 (dd, J=3.8, 4.9 Hz, 1H), 6.99 (s, 1H), 6.91 (d, J=7.9 Hz), 3.92 (s, 6H).

Example 9

4-((2-Methoxy-4-pyridinyl)methylene)-2-(2-thienyl)-5(4H)-oxazolone

[Formula 17]

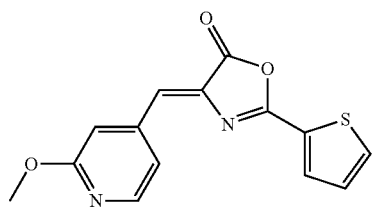

A mixture of N-(2-thienylcarbonyl)glycine (454 mg, 2.45 mmol), 2-methoxy-4-pyridinecarboxaldehyde (370 mg, 2.7 mmol), sodium acetate (201 mg, 2.45 mmol) and acetic anhydride (3.0 mL) was stirred at 90° C. for 3 hours in a sealed tube. Thereafter, the temperature of the reaction solution was returned to room temperature, and water (15 mL) was then added thereto. The obtained mixture was stirred at the same temperature as described above for 1 hour. Thereafter, the precipitated crystal was collected by filtration, and it was washed with water (50 mL) and was then dried under reduced pressure, so as to obtain 572 mg of the above-captioned compound.

$^1$H-NMR (400 MHz, DMSO-d$_6$, δ).

8.31 (d, J=5.3 Hz, 1H), 8.19 (d, J=5.0 Hz, 1H), 8.04 (d, J=3.7 Hz, 1H), 7.76 (d, J=5.3 Hz, 1H), 7.54 (s, 1H), 7.38 (dd, J=4.9, 3.7 Hz, 1H), 7.21 (s, 1H), 3.90 (s, 3H).

ESI-MS m/z 287 (M+H)$^+$.

Example 10

4-((1-Methyl-1H-imidazol-yl)methylene)-2-(2-thienyl)-5(4H)-oxazolone

[Formula 18]

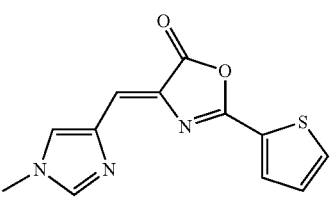 [SMILES: Cn1cnc(/C=C2\N=C(c3cccs3)OC2=O)c1]

To a screw-capped test tube, N-(2-thienylcarbonyl)glycine (56 mg, 0.3 mmol), 1-methylimidazol-4-carboxaldehyde (36 mg, 0.3 mmol), sodium acetate (25 mg, 0.3 mmol) and acetic anhydride (0.3 mL) were added. The test tube was sealed, and it was then stirred at an external temperature of 90° C. Three hours later, the temperature of the reaction solution was returned to room temperature, and water (1.5 mL) was then added thereto. The obtained mixture was stirred at the same temperature as described above for 1.5 hours. Thereafter, the precipitated crystal was collected by filtration, and it was washed with water (5 mL) and was then dried under reduced pressure, so as to obtain 16 mg of the above-captioned compound.

$^1$H-NMR (400 MHz, DMSO-d$_6$, δ).

8.16 (s, 1H), 8.09 (d, J=4.9 Hz, 1H), 7.95 (d, J=3.8 Hz, 1H), 7.83 (s, 1H), 7.34 (dd, J=4.8, 3.8 Hz, 1H), 7.09 (s, 1H), 3.80 (s, 3H).

ESI-MS m/z 260 (M+H)$^+$.

Example 11

4-((5-Acetyloxymethyl-2-furanyl)methylene)-2-(2-thienyl)-5(4H)-oxazolone

[Formula 19]

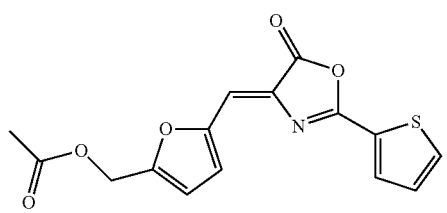

To a screw-capped test tube, N-(2-thienylcarbonyl)glycine (100 mg, 0.54 mmol), 5-hydroxymethylfuran-2-aldehyde (61 μL, 0.6 mmol), sodium acetate (45 mg, 0.54 mmol) and acetic anhydride (0.32 mL) were added. The test tube was sealed, and it was then stirred at an external temperature of 90° C. Three hours later, the temperature of the reaction solution was returned to room temperature, and water (1.5 mL) was then added thereto. The reaction mixture was extracted with ethyl acetate (5 mL) twice, and organic layers were then gathered. The thus obtained organic layer was washed with water (5 mL) twice, and then with a saturated saline (5 mL) once. Thereafter, the resultant was dried over anhydrous sodium sulfate and was then filtered, followed by vacuum concentration. The obtained residue was purified by medium-pressure silica gel chromatography (hexane:ethyl acetate=9:1→4:6) and was then dried under reduced pressure, so as to obtain 31 mg of the above-captioned compound.

$^1$H-NMR (400 MHz, DMSO-$d_6$, δ).

8.12 (d, J=4.1 Hz, 1H), 7.96 (d, J=4.1 Hz, 1H), 7.46 (d, J=3.4 Hz, 1H), 7.35 (d, J=4.6 Hz, 1H), 7.12 (s, 1H), 6.84 (d, J=3.4 Hz, 1H), 5.15 (s, 2H), 2.09 (s, 3H).

ESI-MS m/z 318 (M+H)$^+$.

Example 12

4-((5-Methoxymethyl-2-furanyl)methylene)-2-(2-thienyl)-5(4H)-oxazolone

[Formula 20]

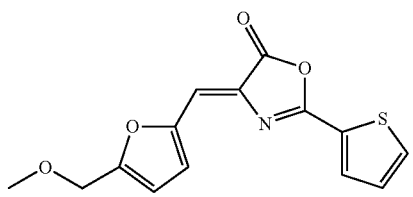 [SMILES: COCc1ccc(/C=C2\N=C(c3cccs3)OC2=O)o1]

To a screw-capped test tube, N-(2-thienylcarbonyl)glycine (56 mg, 0.3 mmol), 5-(methoxymethyl)-2-furancarboxaldehyde (46 mg, 0.3 mmol), sodium acetate (25 mg, 0.3 mmol) and acetic anhydride (0.3 mL) were added. The test tube was sealed, and it was then stirred at an external temperature of 90° C. Three hours later, the temperature of the reaction solution was returned to room temperature, and water (1.5 mL) was then added thereto. The obtained mixture was stirred at the same temperature as described above for 1.5 hours. Thereafter, the precipitated crystal was collected by filtration, and it was washed with water (5 mL) and was then dried under reduced pressure, so as to obtain 44 mg of the above-captioned compound.

$^1$H-NMR (400 MHz, DMSO-$d_6$, δ).

8.12 (d, J=4.9 Hz, 1H), 7.95 (d, J=4.9 Hz, 1H), 7.46 (d, J=3.4 Hz, 1H), 7.34 (dd, J=3.4, 4.9 Hz, 1H), 7.13 (s, 1H), 6.77 (d, J=3.5 Hz, 1H), 4.47 (s, 2H), 3.33 (s, 3H).

ESI-MS m/z 290 (M+H)$^+$.

Example 13

4-((4-Oxazoyl)methylene)-2-(2-thienyl)-5(4H)-oxazolone

[Formula 21]

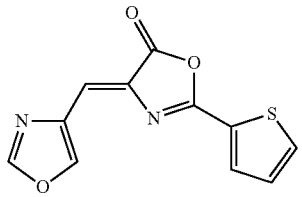 [SMILES: O=C1OC(c2cccs2)=N/C1=C\c1cocn1]

To a screw-capped test tube, N-(2-thienylcarbonyl)glycine (56 mg, 0.3 mmol), 4-oxazolecarboxaldehyde (32 mg, 0.3 mmol), sodium acetate (25 mg, 0.3 mmol) and acetic anhydride (0.3 mL) were added. The test tube was sealed, and it was then stirred at an external temperature of 90° C. Three hours later, the temperature of the reaction solution was returned to room temperature, and water (1.5 mL) was then added thereto. The obtained mixture was stirred at the same temperature as described above for 1.5 hours. Thereafter, the precipitated crystal was collected by filtration, and it was washed with water (5 mL) and was then dried under reduced pressure, so as to obtain 26 mg of the above-captioned compound.

$^1$H-NMR (400 MHz, DMSO-$d_6$, δ).

8.86 (s, 1H), 8.60 (s, 1H), 8.16 (d, J=4.9 Hz, 1H), 8.05 (d, J=3.8 Hz, 1H), 7.36 (dd, J=3.8, 4.9 Hz, 1H), 7.07 (s, 1H).

ESI-MS m/z 247 (M+H)$^+$.

Example 14

4-((1,2,3-Thiadiazol-4-yl)methylene)-2-(2-thienyl)-5(4H)-oxazolone

[Formula 22]

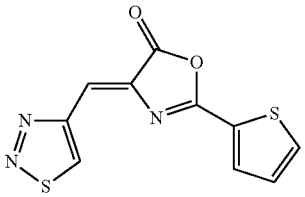 [SMILES: O=C1OC(c2cccs2)=N/C1=C\c1csnn1]

To a screw-capped test tube, N-(2-thienylcarbonyl)glycine (56 mg, 0.3 mmol), 1,2,3-thiadiazol-4-carboxaldehyde (37 mg, 0.3 mmol), sodium acetate (25 mg, 0.3 mmol) and acetic anhydride (0.3 mL) were added. The test tube was sealed, and it was then stirred at an external temperature of 90° C. Three hours later, the temperature of the reaction solution was returned to room temperature, and water (1.5 mL) was then added thereto. The obtained mixture was stirred at the same temperature as described above for 1.5 hours. Thereafter, the precipitated crystal was collected by filtration, and it was washed with water (5 mL) and was then dried under reduced pressure, so as to obtain 30 mg of the above-captioned compound.

¹H-NMR (400 MHz, DMSO-d₆, δ).
9.92 (s, 1H), 8.21 (d, J=4.9 Hz, 1H), 8.07 (d, J=3.7 Hz, 1H), 7.73 (s, 1H), 7.39 (dd, J=3.7, 4.8 Hz, 1H).

Example 15

4-((1,5-Dimethyl-1H-pyrazol-4-yl)methylene)-2-(2-thienyl)-5(4H)-oxazolone

[Formula 23]

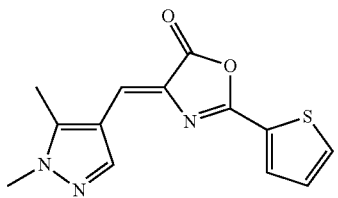

To a screw-capped test tube, N-(2-thienylcarbonyl)glycine (56 mg, 0.3 mmol), 1,5-dimethyl-1H-pyrazol-4-carboxaldehyde (41 mg, 0.3 mmol), sodium acetate (25 mg, 0.3 mmol) and acetic anhydride (0.3 mL) were added. The test tube was sealed, and it was then stirred at an external temperature of 90° C. Three hours later, the temperature of the reaction solution was returned to room temperature, and water (1.5 mL) was then added thereto. The obtained mixture was stirred at the same temperature as described above for 1.5 hours. Thereafter, the precipitated crystal was collected by filtration, and it was washed with water (5 mL) and was then dried under reduced pressure, so as to obtain 35 mg of the above-captioned compound.

¹H-NMR (400 MHz, DMSO-d₆, δ).
8.34 (s, 1H), 8.04 (d, J=4.9 Hz, 1H), 7.90 (d, J=3.7 Hz, 1H), 7.32 (dd, J=3.8, 4.9 Hz, 1H), 7.19 (s, 1H), 3.81 (s, 3H), 2.45 (s, 3H).
ESI-MS m/z 274 (M+H)⁺.

Example 16

4-((1,3-Dimethyl-1H-pyrazol-4-yl)methylene)-2-(2-thienyl)-5(4H)-oxazolone

[Formula 24]

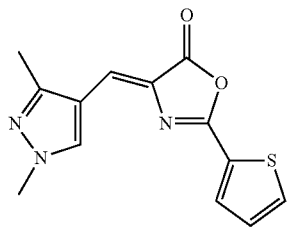

To a screw-capped test tube, N-(2-thienylcarbonyl)glycine (56 mg, 0.3 mmol), 1,3-dimethyl-1H-pyrazol-4-carboxaldehyde (41 mg, 0.3 mmol), sodium acetate (25 mg, 0.3 mmol) and acetic anhydride (0.3 mL) were added. The test tube was sealed, and it was then stirred at an external temperature of 90° C. Three hours later, the temperature of the reaction solution was returned to room temperature, and water (1.5 mL) was then added thereto. The obtained mixture was stirred at the same temperature as described above for 1.5 hours. Thereafter, the precipitated crystal was collected by filtration, and it was washed with water (5 mL) and was then dried under reduced pressure, so as to obtain 24 mg of the above-captioned compound.

¹H-NMR (400 MHz, DMSO-d₆, δ).
8.51 (s, 1H), 8.07 (d, J=4.9 Hz, 1H), 7.93 (d, J=3.7 Hz, 1H), 7.33 (dd, J=3.8, 4.9 Hz, 1H), 7.12 (s, 1H), 3.89 (s, 3H), 2.32 (s, 3H).
ESI-MS m/z 274 (M+H)⁺.

Example 17

4-((2,6-Dimethoxy-3-pyridinyl)methylene)-2-(2-thienyl)-5(4H)-oxazolone

[Formula 25]

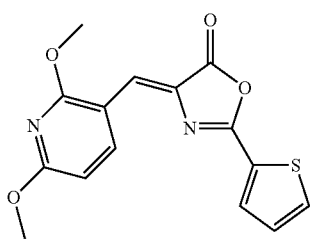

To a sealed tube, 2,6-dimethoxypyridin-3-carboxaldehyde (368 mg, 2.2 mmol), glycine thiophene amide (374 mg, 2.0 mmol), sodium acetate (anhydrous) (165 mg, 2.0 mmol) and acetic anhydride (3.0 mL) were added. The obtained mixture was stirred at 90° C. for 3 hours in the sealed tube. Thereafter, the temperature of the reaction solution was cooled to room temperature, and water (15 mL) was then added thereto while cooling on ice. The mixture was stirred at room temperature for 1 hour, and a crystal was then collected by filtration. The crystal was washed with water (50 mL), and was then dried under reduced pressure, so as to obtain 385 mg of the above-captioned compound.

¹H-NMR (400 MHz, DMSO-d₆, δ).
8.91 (d, J=8.6 Hz, 1H), 8.09 (d, J=4.9 Hz, 1H), 7.93 (d, J=3.8 Hz, 1H), 7.34 (dd, J=4.8, 3.9 Hz, 1H), 7.30 (s, 1H), 6.66 (d, J=8.5 Hz, 1H), 4.02 (s, 3H), 3.97 (s, 3H).
ESI-MS m/z 317 (M+H)⁺.

Example 18

4-((6-Methoxy-2-methyl-3-pyridinyl)methylene)-2-(2-thienyl)-5(4H)-oxazolone

[Formula 26]

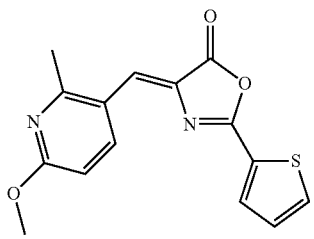 [SMILES: COc1ccc(/C=C2\N=C(c3cccs3)OC2=O)c(C)n1]

(18-1)
2-Methoxy-6-methylpyridine (10 mL, 81 mmol) was suspended in a 0.15 mol//L disodium hydrogen phosphate aqueous solution (160 mL). Thereafter, a solution prepared by suspending bromine (4.15 mL, 81 mmol) in a 0.15 mol//L disodium hydrogen phosphate aqueous solution (160 mL) was added dropwise to the suspension at room temperature over 1 hour. The reaction solution was stirred at the same temperature as described above overnight. Thereafter, the reaction solution was extracted with methylene chloride (300 mL) three times. Organic layers were gathered. The resultant was dried over anhydrous magnesium sulfate and was then filtrated, followed by vacuum concentration. The obtained residue was distilled away under reduced pressure (91° C.-96° C./16 mmHg), so as to obtain 9.47 g of 3-bromo-6-methoxy-2-methyl-pyridine.

(18-2)

The 3-bromo-6-methoxy-2-methyl-pyridine (2.0 g, 9.9 mmol) obtained in (18-1) above was dissolved in toluene (dehydrated) (50 mL), and thereafter, n-butyllithium (6.4 mL, 10 mmol, 1.57 mmol/L hexane solution) was added dropwise to the solution at −78° C. in an argon atmosphere. The obtained mixture was stirred at the same temperature as described above for 30 minutes, and DMF (3.0 mL) was then added to the reaction solution. The obtained mixture was further stirred for 30 minutes. Thereafter, a saturated ammonium chloride water (100 mL) was slowly added to the reaction solution, and the temperature of the mixture was then increased to room temperature. The mixture was extracted with diethyl ether (100 mL) three times, and organic layers were gathered. The resultant was washed with water (100 mL) and saturated saline (100 mL), and was dried over anhydrous sodium sulfate and was then filtrated, followed by vacuum concentration. The obtained residue was purified by silica gel column chromatography (SiO$_2$ 30 g, hexane:ethyl acetate=98:2 to 90:10), so as to obtain 487 mg of 6-methoxy-2-methyl-3-pyridinecarboxaldehyde.

(18-3)

The 6-methoxy-2-methyl-3-pyridinecarboxaldehyde (333 mg, 2.2 mmol) obtained in (18-2) above, glycine thiophene amide (374 mg, 2.0 mmol), sodium acetate (anhydrous) (165 mg, 2.0 mmol) and acetic anhydride (3.0 mL) were added to a sealed tube, and the obtained mixture was then stirred at 90° C. for 3 hours in the sealed tube. Thereafter, the reaction solution was cooled to room temperature, and water (15 mL) was then added thereto while cooling on ice. The mixture was stirred at room temperature for 1 hour, and a crystal was then collected by filtration. The crystal was washed with water (50 mL) and was then dried under reduced pressure, so as to obtain 275 mg of the above-captioned compound.

$^1$H-NMR (400 MHz, DMSO-d$_6$, δ).

8.91 (d, J=8.8 Hz, 1H), 8.12 (d, J=5.0 Hz, 1H), 7.96 (d, J=3.9 Hz, 1H), 7.34 (dd, J=4.8, 3.9 Hz, 1H), 7.29 (s, 1H), 6.89 (d, J=8.8 Hz, 1H), 3.92 (s, 3H), 2.63 (s, 3H).

ESI-MS m/z 301 (M+H)$^+$.

Example 19

4-((2-Chloro-6-methoxy-3-pyridinyl)methylene)-2-(2-thienyl)-5(4H)-oxazolone

[Formula 27]

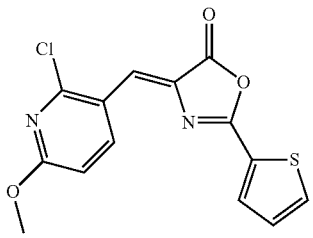 [SMILES: COc1ccc(/C=C2\N=C(c3cccs3)OC2=O)c(Cl)n1]

(19-1)

2-Chloro-6-methylpyridine (0.96 mL, 8.1 mmol) was suspended in a 0.15 mol/L disodium hydrogen phosphate aqueous solution (16 mL). Thereafter, a solution prepared by suspending bromine (0.46 mL, 8.9 mmol) in a 0.15 mol//L disodium hydrogen phosphate aqueous solution (16 mL) was added dropwise to the suspension at room temperature over 1 hour. The reaction solution was stirred at the same temperature as described above overnight. Thereafter, the reaction solution was extracted with methylene chloride (30 mL) three times. Organic layers were gathered. The resultant was dried over anhydrous magnesium sulfate and was then filtrated, followed by vacuum concentration. The obtained residue was purified by silica gel column chromatography (SiO$_2$ 30 g, hexane:ethyl acetate=99:1 to 95:5), so as to obtain 506 mg of 3-bromo-2-chloro-6-methoxy-pyridine.

(19-2)

The 3-bromo-2-chloro-6-methoxy-pyridine (0.50 g, 2.26 mmol) obtained in (19-1) above was dissolved in toluene (dehydrated) (11 mL), and thereafter, n-butyllithium (1.46 mL, 2.3 mmol, 1.57 mmol/L hexane solution) was added dropwise to the solution at −78° C. in an argon atmosphere. The obtained mixture was stirred at the same temperature as described above for 30 minutes, and DMF (1.0 mL) was then added to the reaction solution. The obtained mixture was further stirred for 30 minutes. Thereafter, a saturated ammonium chloride water (20 mL) was slowly added to the reaction solution, and the temperature of the mixture was then increased to room temperature. The mixture was extracted with diethyl ether (20 mL) twice, and organic layers were gathered. The resultant was dried over anhydrous sodium sulfate and was then filtrated, followed by vacuum concentration. The obtained residue was purified by silica gel column chromatography (SiO$_2$ 30 g, hexane:ethyl acetate=95:5 to 80:20), so as to obtain 180 mg of 2-chloro-6-methoxy-3-pyridinecarboxaldehyde.

(19-3)

The 2-chloro-6-methoxy-3-pyridinecarboxaldehyde (137 mg, 0.8 mmol) obtained in (19-2) above, glycine thiophene amide (148 mg, 0.8 mmol), sodium acetate (anhydrous) (66 mg, 0.8 mmol) and acetic anhydride (1.5 mL) were added to a sealed tube, and the obtained mixture was then stirred at 90° C. for 3 hours in the sealed tube. Thereafter, the reaction solution was cooled to room temperature, and water (10 mL) was then added thereto while cooling on ice. The mixture was stirred at room temperature for 1 hour, and a crystal was then collected by filtration. The crystal was washed with water (50 mL) and was then dried under reduced pressure to obtain 213 mg of a rough crystal. Thereafter, 100 mg of the obtained rough crystal was purified by silica gel column chromatography (SiO$_2$ 10 g, hexane:ethyl acetate=95:5 to 80:20), so as to obtain 55 mg of the above-captioned compound.

$^1$H-NMR (400 MHz, DMSO-d$_6$, δ).

9.04 (d, J=8.7 Hz, 1H), 8.16 (d, J=4.9 Hz, 1H), 8.01 (d, J=3.8 Hz, 1H), 7.37 (dd, J=4.7, 3.9 Hz, 1H), 7.26 (s, 1H), 7.13 (d, J=8.7 Hz, 1H), 3.94 (s, 3H). ESI-MS m/z 321 (M+H)$^+$.

Experimental Examples

1. Inhibitory Action of Oxazolone Derivative to Inhibit Casein Kinase 1δ and Casein Kinase 1ε

The activity of the present compound to inhibit casein kinase 1δ and casein kinase 1ε was measured using human recombinant casein kinase 1δ (INVITROGEN; Cat No. PV3665) or casein kinase 1ε (INVITROGEN; Cat No. PV3500) as an enzyme source, and using Z'-LYTE Ser/Thr 11

Peptide (INVITROGEN; Cat No. PV3671) as a phosphorylation substrate. The compositions (final concentrations) applied during the inhibitory activity measurement assays are as follows.

Assay of Casein Kinase 1δ

3.0 μg/ml casein kinase 1δ, 0.3 μg/ml the present compound, 1.0 μM peptide, 20 μM ATP, 50 mM HEPES (pH 7.4), 10 mM $MgCl_2$, 0.01% Brij-35, and 0.5% DMSO Assay of Casein Kinase 1ε

0.5 μg/ml casein kinase 1δ, 0.3 μg/ml the present compound, 1.0 μM peptide, 20 μM ATP, 50 mM HEPES (pH 7.4), 10 mM $MgCl_2$, 0.01% Brij-35, and 0.5% DMSO The present compound had previously been reacted with the enzyme at room temperature for 15 minutes. Two hours after completion of the reaction, the remaining phosphorylation activity was measured using Z'-LYTE Kinase Assay Kit-Ser/Thr 11 Peptide (INVITROGEN; Cat No. PV3670).

The inhibitory rate of the present compound was calculated with respect to the phosphorylation activity of each of casein kinase 1δ and casein kinase 1ε in a case in which no such compounds were added. Tables 1 to 4 show the inhibitory rate (%) of each compound.

TABLE 1

| Structural formula | Compound name | Casein kinase 1δ inhibitory rate | Casein kinase 1ε inhibitory rate |
|---|---|---|---|
| | 2-(4-Bromo-3-methylphenyl)-4-(3-pyridinylmethylene)-5(4H)-oxazolone [or 2-(4-Bromo-3-methylphenyl)-4-(pyridine-3-ylmethylene)oxazol-5(4H)-one] | 83.2% | 97.8% |
| | 2-(3-Bromo-4-methoxyphenyl)-4-(3-pyridinylmethylene)-5-(4H)-oxazolone | 94.2% | 99.4% |
| | 2-(2-phenylethenyl)-4-(3-pyridinylmethylene)-5(4H)-oxazolone | 85.0% | 83.4% |
| | 2-(5-Methyl-2-thienyl)-4-(3-pyridinylmethylene)-5(4H)-oxazolone | 95.5% | 97.5% |
| | 4-((4-methoxyphenyl)methylene)-2-(2-thienyl)-5(4H)-oxazolone | 96.1% | 98.6% |

TABLE 1-continued

| Structural formula | Compound name | Casein kinase 1δ inhibitory rate | Casein kinase 1ε inhibitory rate |
|---|---|---|---|
| | Methyl 4-((5-oxo-2-(2-thienyl)oxazol-4(5H)-ylidene)methyl) benzoate | 86.8% | 95.1% |

TABLE 2

| Structural formula | Compound name | Casein kinase 1δ inhibitory rate | Casein kinase 1ε inhibitory rate |
|---|---|---|---|
| | 4-((4-Methoxy-3-nitrophenyl)methylene)-2-(2-thienyl)-5(4H)-oxazolone | 91.0% | 94.8% |
| | 4-((6-Chloro-1,3-benzodioxol-5-yl)methylene)-2-(2-thienyl)-5(4R)-oxazolone | 74.3% | 97.0% |
| | 4-((3-Chloro-4-nitrophenyl)methylene)-2-(2-thienyl)-5(4H)-oxazolone | 87.6% | 97.6% |
| | 4-((3-Bromo-4-nitrophenyl)methylene)-2-(2-thienyl)-5(4H)-oxazolone | 85.9% | 94.4% |

TABLE 2-continued

| Structural formula | Compound name | Casein kinase 1δ inhibitory rate | Casein kinase 1ε inhibitory rate |
| --- | --- | --- | --- |
|  | 4-((8-Chloro-2,3-dihydro-1,4-benzodioxin-6-yl)methylene)-2-(2-thienyl)-5(4H)-oxazolone | 76.7% | 85.8% |
|  | 4-((1-Methyl-1H-pyrazol-4-yl)methylene)-2-(2-thienyl)-5(4H)-oxazolone | 73.6% | 48.8% |

TABLE 3

| Structural formula | Compound name | Casein kinase 1δ inhibitory rate | Casein kinase 1ε inhibitory rate |
| --- | --- | --- | --- |
|  | 4-((5-Methoxy-3-pyridinyl)methylene)-2-(5-methyl-2-thienyl)-5(4H)-oxazolone | 82.0% | 97.1% |
|  | 4-((5-Methoxy-3-pyridinyl)methylene)-2-(2-thienyl)-5(4H)-oxazolone | 91.1% | 96.6% |
|  | 4-((5-Fluoro-3-pyridinyl)methylene)-2-(2-thienyl)-5(4H)-oxazolone | 87.4% | 92.1% |

TABLE 3-continued

| Structural formula | Compound name | Casein kinase 1δ inhibitory rate | Casein kinase 1ε inhibitory rate |
| --- | --- | --- | --- |
|  | 4-((2-Fluoro-3-pyridinyl)methylene)-2-(2-thienyl)-5(4H)-oxazolone | 65.6% | 39.2% |
|  | 4-((6-Methoxy-3-pyridinyl)methylene)-2-(2-thienyl)-5(4H)-oxazolone | 86.3% | 95.6% |
|  | 4-((2-Methoxy-4-pyridinyl)methylene)-2-(2-thienyl)-5(4H)-oxazolone | 60.5% | 93.8% |
|  | 4-((1-Methyl-1H-imidazol-4-yl)methylene)-2-(2-thienyl)-5(4H)-oxazolone | 37.0% | 18.1% |
|  | 4-((5-Methoxymethyl-2-furanyl)methylene)-2-(2-thienyl)-5(4H)-oxazolone | 29.0% | 9.0% |
|  | 4-((4-Oxazoyl)methylene)-2-(2-thienyl)-5(4H)-oxazolone | 67.9% | 32.0% |
|  | 4-((1,2,3-Thiadazol-4-yl)methylene)-2-(2-thienyl)-5(4H)-oxazolone | 32.2% | 19.2% |

TABLE 4

| Structural formula | Compound name | Casein kinase 1δ inhibitory rate | Casein kinase 1ε inhibitory rate |
|---|---|---|---|
| | 4-((6-Methoxy-2-methyl-3-pyridinyl)methylene)-2-(2-thienyl)-5(4H)-oxazolone | 55.3% | 32.8% |
| | 4-((2-Chloro-6-methoxy-3-pyridinyl)methylene)-2-(2-thienyl)-5(4H)-oxazolone | 76.1% | 52.5% |

The inhibitory specificity of each of the casein kinase 1δ and casein kinase 1ε inhibitory compounds to various types of kinases was examined using Profiler Pro kit (manufactured by Caliper Life Sciences, Inc.) in accordance with the method described in the attached document. Each of the compounds shown in Tables 1 to 4 was allowed to react with each of various types of kinases for 15 minutes so as to result in a final concentration of 10 μM. After completion of the reaction, enzyme activity was analyzed. As a result, there were found no effective inhibitory activity (25% or more of inhibitory activity) on various types of kinases regarding which the expression of side effects due to enzyme inhibition had been concerned (MAPKAPK2, AurA, PKCξ, RSK1, PRAK, Erk1, PKD2, CHK1, ABL, FYN, LYN, CHK2, MET, LCK, SRC, GSK3β, Erk2, PKA, AKT2, INSR, p38α, AKT1, MSK1, PKCβ2, ROCK2, CDK2, MST2, PKG1α, PAK2, IGF1R, FGFR1, MARK1, CAMK2δ, PIM2, BTK, c-TAK1, CAMK4, AMPK, FLT3, HGK, VEGFR2, KDR, c-RAF, P70S6K, IRAK4, SGK1, and SYK). Thus, the present compounds were found to be inhibitory compounds exhibiting high selectivity to casein kinase 1δ and casein kinase 1ε.

2. Concerning Effectiveness of the Compound of the Present Invention

The effectiveness of the casein kinase 1δ and casein kinase 1ε inhibitory compound on circadian rhythm disorder can be demonstrated using the following animal models. That is to say, rats are acclimated for one or more weeks under light/dark (LD) conditions consisting of a light period of 12 hours and a dark period of 12 hours. On the 9$^{th}$ hour of the light period, the inhibitory compound mixed with a solubilizer (carboxymethyl cellulose, etc.) is administered to the rats orally or intraperitoneally. After the administration, a change in the free-running period is observed over time. The effectiveness of the present compound can be demonstrated by the fact that the phase of the free-running period moves forward or backward, when compared with the case of administering only the solubilizer.

The effectiveness of the casein kinase 1δ and casein kinase 1ε inhibitory compound on central neurodegenerative disease can be demonstrated using the following animal models. That is to say, using transgenic mice that excessively express in their brain a mutated tau protein causing neurofibrillary degeneration, the inhibitory compound was administered to the transgenic mice for a long period of time by mixing it into their feed or drinking water. The effectiveness of the present compound can be demonstrated by pathologically examining the fact that the degree of occurrence of synapse disappearance or neurological deficit is decreased, when compared with a non-administration group.

The effectiveness of the casein kinase 1δ and casein kinase 1ε inhibitory compound on pancreatic cancer can be demonstrated using the following animal models. That is to say, a human pancreatic cancer cell line (approximately 5,000,000 cells) is cultured in vitro, and the culture is then subcutaneously injected into the back of SCID mice. From 14 days after completion of the injection, the inhibitory compound mixed with a solubilizer (carboxymethyl cellulose, etc.) is administered to the mice orally or intraperitoneally. The size of a tumor in the subcutis is observed day by day. On the 10$^{th}$ day after the administration, the tumor is excised from the subcutis, and the weight thereof is then measured, so as to demonstrate the effectiveness of the inhibitory agent.

INDUSTRIAL APPLICABILITY

The inhibitor of casein kinase 1δ and casein kinase 1ε of the present invention and the pharmaceutical agent of the present invention comprising the above-described inhibitor as an active ingredient greatly contribute to the development of a pharmaceutical agent useful for the treatment and/or prevention of diseases, with the pathological conditions of which the activation of the casein kinase 1δ or casein kinase 1ε is associated. In particular, the present inhibitor of casein kinase 1δ and casein kinase 1ε and the present pharmaceutical agent greatly contribute to the development of a pharmaceutical agent useful for the treatment and/or prevention of cir-

The invention claimed is:

1. A method for treating a disease, with the pathological condition of which the activation of casein kinase 1δ or casein kinase 1ε is associated, comprising:

administering to a subject at least one of an oxazolone derivative represented by the following general formula (1), a salt thereof, a solvate thereof, or a hydrate thereof:

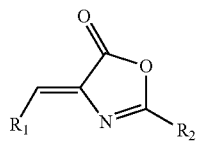
(1)

wherein in the formula (1), $R_1$ represents any one of:

(i) a substituted or unsubstituted 6-membered heterocyclic group optionally having a condensed ring, which is represented by the following formula (2):

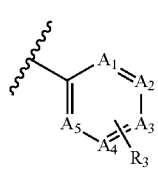
(2)

(ii) a substituted or unsubstituted 5-membered heterocyclic group optionally having a condensed ring, which is represented by the following formula (3a) or (3b):

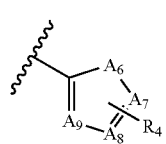
(3a)

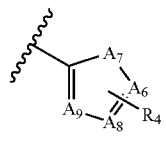
(3b)

(iii) a substituted or unsubstituted aromatic hydrocarbon group optionally having a condensed ring, which is represented by the following formula (4):

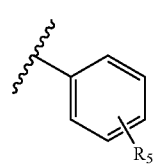
(4)

(iv) a substituted or unsubstituted aromatic hydrocarbon lower alkyl group or aromatic hydrocarbon lower alkenyl group optionally having a condensed ring, which is represented by the following formula (5):

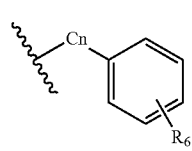
(5)

wherein, in the formula (2), each of $A_1$ to $A_5$ independently represents a carbon atom or a nitrogen atom;

wherein, in the formula (2), $R_3$ represents 1 to 5 identical or different substituents on $A_1$ to $A_5$, each of which independently represents a hydrogen atom, a halogen atom selected from the group consisting of a fluorine atom, a bromine atom and an iodine atom, a hydroxyl group, a nitro group, a cyano group, a carboxy group, a lower alkoxy group, a lower alkoxyalkyl group, a lower alkoxycarbonyl group, a lower acyl group, a lower acyloxy group, a lower acyloxyalkyl group, a carbamoyl group, a sulfamoyl group, a trifluoromethyl group, a substituted or unsubstituted allyl group, a substituted or unsubstituted heteroallyl group, a substituted or unsubstituted phenoxy group, a substituted or unsubstituted amino group, a substituted or unsubstituted lower alkyl group selected from the group consisting of methyl, ethyl, propyl, isopropyl, butyl, isobutyl, isopentyl and neopentyl, a substituted or unsubstituted lower alkenyl group, a substituted or unsubstituted aromatic hydrocarbon group, or a substituted or unsubstituted aromatic heterocyclic group;

wherein, in the formula (2), if there are a plurality of substituents, a ring may be formed by such a plurality of substituents;

wherein in the formula (3a) or (3b), $A_6$ represents an oxygen atom, a sulfur atom or a nitrogen atom;

wherein, in the formula (3a) or (3b), $A_7$, $A_8$ and $A_9$ each represent a carbon atom or a nitrogen atom;

wherein, in the formula (3a) or (3b), $R_4$ represents 1 to 4 identical or different substituents on $A_6$ to $A_9$, each of which independently represents a hydrogen atom, a halogen atom, a hydroxyl group, a nitro group, a cyano group, a carboxy group, a lower alkoxy group, a lower alkoxyalkyl group, a lower alkoxycarbonyl group, a lower acyl group, a lower acyloxy group, a lower acyloxyalkyl group, a carbamoyl group, a sulfamoyl group, a trifluoromethyl group, a substituted or unsubstituted allyl group, a substituted or unsubstituted heteroallyl group, a substituted or unsubstituted phenoxy group, a substituted or unsubstituted amino group, a substituted or unsubstituted lower alkyl group, a substituted or unsubstituted lower alkenyl group, a substituted or unsubstituted aromatic hydrocarbon group, or a substituted or unsubstituted aromatic heterocyclic group;

wherein, in the formula (4), $R_5$ represents 1 to 5 identical or different substituents on a benzene ring, each of which independently represents a hydrogen atom, a halogen atom, a hydroxyl group, a nitro group, a cyano group, a carboxy group, a lower alkoxy group, a lower alkoxyalkyl group, a lower alkoxycarbonyl group, a lower acyl group, a lower acyloxy group, a lower acyloxyalkyl group, a carbamoyl group, a sulfamoyl group, a trifluoromethyl group, a substituted or unsubstituted allyl group, a substituted or unsubstituted heteroallyl group, a substituted or unsubstituted phenoxy group, a substituted or unsubstituted amino group, a substituted or unsubstituted lower alkyl group, a substituted or unsubstituted lower alkenyl group, a substituted or unsubstituted aromatic hydrocarbon group, or a substituted or unsubstituted aromatic heterocyclic group;

wherein, in the formula (4), if there are a plurality of substituents, a ring may be formed by such a plurality of substituents;

wherein in the formula (5), n represents an integer of 1 to 10 and a lower alkyl portion or lower alkenyl portion represented by Cn may be any one of a linear portion, a branched portion, a cyclic portion and a combination thereof, containing 1 to 10 carbon atoms;

wherein, in the formula (5), $R_6$ represents 1 to 5 identical or different substituents on a benzene ring, each of which independently represents a hydrogen atom, a halogen atom, a hydroxyl group, a nitro group, a cyano group, a carboxy group, a lower alkoxy group, a lower alkoxyalkyl group, a lower alkoxycarbonyl group, a lower acyl group, a lower acyloxy group, a lower acyloxyalkyl group, a carbamoyl group, a sulfamoyl group, a trifluoromethyl group, a substituted or unsubstituted allyl group, a substituted or unsubstituted heteroallyl group, a substituted or unsubstituted phenoxy group, a substituted or unsubstituted amino group, a substituted or unsubstituted lower alkyl group, a substituted or unsubstituted lower alkenyl group, a substituted or unsubstituted aromatic hydrocarbon group, or a substituted or unsubstituted aromatic heterocyclic group, wherein, in the formula (5), if there are a plurality of substituents, a ring may be formed by such a plurality of substituents; wherein $R_2$ represents any one of formula (2), (3a), (3b), or (5)

wherein the disease is a circadian rhythm sleep disorder or depressive disorder, and wherein the subject is a subject in need of treatment of circadian rhythm sleep disorder or depressive disorder.

2. The method according to claim 1,
wherein $R_1$ represents a substituted or unsubstituted pyridinyl group, and
wherein $R_2$ represents a substituted or unsubstituted aromatic hydrocarbon lower alkyl group or aromatic hydrocarbon lower alkenyl group optionally having a condensed ring, which is represented by the formula (5).

3. The method according to claim 2, wherein the compound represented by the general formula (1) is 2-(2-phenylethenyl)-4-(3-pyridinylmethylene)-5(4H)-oxazolone.

4. The method according to claim 1,
wherein $R_1$ represents a substituted or unsubstituted pyridinyl group, and
wherein $R_2$ represents a substituted or unsubstituted 5-membered heterocyclic group, which is represented by the formula (3a) or (3b).

5. The method according to claim 4,
wherein $R_1$ represents a substituted or unsubstituted pyridinyl group, and
wherein $R_2$ represents a substituted or unsubstituted thiophenyl group.

6. The method according to claim 5, wherein the compound represented by the general formula (1) is selected from the group consisting of:
2-(5-methyl-2-thienyl)-4-(3-pyridinylmethylene)-5(4H)-oxazolone,
4-((5-methoxy-3-pyridinyl)methylene)-2-(5-methyl-2-thienyl)-5(4H)-oxazolone,
4-((5-methoxy-3-pyridinyl)methylene)-2-(2-thienyl)-5(4H)-oxazolone,
4-((5-fluoro-3-pyridinyl)methylene)-2-(2-thienyl)-5(4H)-oxazolone,
4-((2-fluoro-3-pyridinyl)methylene)-2-(2-thienyl)-5(4H)-oxazolone,
4-((6-methoxy-3-pyridinyl)methylene)-2-(2-thienyl)-5(4H)-oxazolone,
4-((6-acetylmethylamino-3-pyridinyl)methylene)-2-(2-thienyl)-5(4H)-oxazolone,
4-((2-dimethylamino-3-pyridinyl)methylene)-2-(2-thienyl)-5(4H)-oxazolone,
4-((6-methoxy-2-pyridinyl)methylene)-2-(2-thienyl)-5(4H)-oxazolone,
4-((2-methoxy-4-pyridinyl)methylene)-2-(2-thienyl)-5(4H)-oxazolone,
4-((2,6-dimethoxy-3-pyridinyl)methylene)-2-(2-thienyl)-5(4H)-oxazolone,
4-((6-methoxy-2-methyl-3-pyridinyl)methylene)-2-(2-thienyl)-5(4H)-oxazolone, and
4-((2-chloro-6-methoxy-3-pyridinyl)methylene)-2-(2-thienyl)-5(4H)-oxazolone.

7. The method according to claim 1,
wherein $R_1$ represents a substituted or unsubstituted aromatic hydrocarbon group optionally having a condensed ring, which is represented by the formula (4), and
wherein $R_2$ represents a substituted or unsubstituted thiophenyl group.

8. The method according to claim 7, wherein the compound represented by the general formula (1) is selected from the group consisting of:
4-((4-methoxyphenyl)methylene)-2-(2-thienyl)-5(4H)-oxazolone,
methyl 4-((5-oxo-2-(2-thienyl)oxazol-4(5H)-ylidene)methyl)benzoate,
4-((4-methoxy-3-nitrophenyl)methylene)-2-(2-thienyl)-5(4H)-oxazolone,
4-((6-chloro-1,3-benzodioxol-5-yl)methylene)-2-(2-thienyl)-5(4H)-oxazolone,
4-((3-chloro-4-nitrophenyl)methylene)-2-(2-thienyl)-5(4H)-oxazolone,
4-((3-bromo-4-nitrophenyl)methylene)-2-(2-thienyl)-5(4H)-oxazolone, and
4-((8-chloro-2,3-dihydro-1,4-benzodioxin-6-yl)methylene)-2-(2-thienyl)-5(4H)-oxazolone.

9. The method according to claim 1,
wherein $R_1$ represents a substituted or unsubstituted 5-membered heterocyclic group, which is represented by the formula (3a) or (3b), and
wherein $R_2$ represents a substituted or unsubstituted thiophenyl group.

10. The method according to claim 9, wherein the compound represented by the general formula (1) is selected from the group consisting of:
4-((1-methyl-1H-pyrazol-4-yl)methylene)-2-(2-thienyl)-5(4H)-oxazolone,
4-((1-methyl-1H-imidazol-4-yl)methylene)-2-(2-thienyl)-5(4H)-oxazolone,
4-((5-acetyloxymethyl-2-furanyl)methylene)-2-(2-thienyl)-5(4H)-oxazolone,
4-((5-methoxymethyl-2-furanyl)methylene)-2-(2-thienyl)-5(4H)-oxazolone,
4-((4-oxazolyl)methylene)-2-(2-thienyl)-5(4H)-oxazolone,
4-((1,2,3-thiadiazol-4-yl)methylene)-2-(2-thienyl)-5(4H)-oxazolone, 4-((1,5-dimethyl-1H-pyrazol-4-yl)methylene)-2-(2-thienyl)-5(4H)-oxazolone, and
4-((1,3-dimethyl-1H-pyrazol-4-yl)methylene)-2-(2-thienyl)-5(4H)-oxazolone.

11. The method according to claim 1, wherein the compound represented by the general formula (1) is 4-((6-methoxy-3-pyridinyl)methylene)-2-(2-thienyl)-5(4H)-oxazolone.

12. A method for treating a disease, with the pathological condition of which the activation of casein kinase 1δ or casein kinase 1ε is associated, comprising:
administering to a subject at least one of an oxazolone derivative represented by the following general formula (1), a salt thereof, a solvate thereof, or a hydrate thereof:

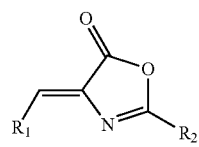

wherein $R_1$ represents a substituted or unsubstituted pyridinyl group, and
wherein $R_2$ represents a substituted or unsubstituted 5-membered heterocyclic group optionally having a condensed ring, which is represented by the formula (3a) or (3b):

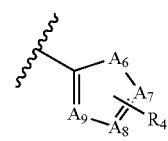

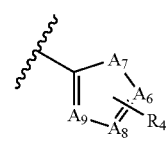

wherein in the formula (3a) or (3b), $A_6$ represents an oxygen atom, a sulfur atom or a nitrogen atom;
wherein, in the formula (3a) or (3b), $A_7$, $A_8$ and $A_9$ each represent a carbon atom or a nitrogen atom;
wherein, in the formula (3a) or (3b), $R_4$ represents 1 to 4 identical or different substituents on $A_6$ to $A_9$, each of which independently represents a hydrogen atom, a halogen atom, a hydroxyl group, a nitro group, a cyano group, a carboxy group, a lower alkoxy group, a lower alkoxyalkyl group, a lower alkoxycarbonyl group, a lower acyl group, a lower acyloxy group, a lower acyloxyalkyl group, a carbamoyl group, a sulfamoyl group, a trifluoromethyl group, a substituted or unsubstituted allyl group, a substituted or unsubstituted heteroallyl group, a substituted or unsubstituted phenoxy group, a substituted or unsubstituted amino group, a substituted or unsubstituted lower alkyl group, a substituted or unsubstituted lower alkenyl group, a substituted or unsubstituted aromatic hydrocarbon group, or a substituted or unsubstituted aromatic heterocyclic group;
wherein, in the formula (3a) or (3b), if there are a plurality of substituents, a ring may be formed by such a plurality of substituents;

wherein the disease is Alzheimer's disease, and
wherein the subject is a subject in need of treatment of Alzheimer's disease.

13. The method according to claim 12,
wherein $R_1$ represents a substituted or unsubstituted pyridinyl group, and
wherein $R_2$ represents a substituted or unsubstituted thiophenyl group.

14. The method according to claim 13, wherein the compound represented by the general formula (1) is selected from the group consisting of:
2-(5-methyl-2-thienyl)-4-(3-pyridinylmethylene)-5(4H)-oxazolone,
4-((5-methoxy-3-pyridinyl)methylene)-2-(5-methyl-2-thienyl)-5(4H)-oxazolone,
4-((5-methoxy-3-pyridinyl)methylene)-2-(2-thienyl)-5(4H)-oxazolone,
4-((5-fluoro-3-pyridinyl)methylene)-2-(2-thienyl)-5(4H)-oxazolone,
4-((2-fluoro-3-pyridinyl)methylene)-2-(2-thienyl)-5(4H)-oxazolone,
4-((6-methoxy-3-pyridinyl)methylene)-2-(2-thienyl)-5(4H)-oxazolone,
4-((6-acetylmethylamino-3-pyridinyl)methylene)-2-(2-thienyl)-5(4H)-oxazolone,
4-((2-dimethylamino-3-pyridinyl)methylene)-2-(2-thienyl)-5(4H)-oxazolone,
4-((6-methoxy-2-pyridinyl)methylene)-2-(2-thienyl)-5(4H)-oxazolone,
4-((2-methoxy-4-pyridinyl)methylene)-2-(2-thienyl)-5(4H)-oxazolone,
4-((2,6-dimethoxy-3-pyridinyl)methylene)-2-(2-thienyl)-5(4H)-oxazolone,
4-((6-methoxy-2-methyl-3-pyridinyl)methylene)-2-(2-thienyl)-5(4H)-oxazolone, and
4-((2-chloro-6-methoxy-3-pyridinyl)methylene)-2-(2-thienyl)-5(4H)-oxazolone.

15. A method for treating a disease, with the pathological condition of which the activation of casein kinase 1δ or casein kinase 1ε is associated, comprising:
administering to a subject at least one of an oxazolone derivative represented by the following general formula (1), a salt thereof, a solvate thereof, or a hydrate thereof:

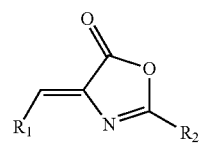

wherein $R_1$ represents a substituted or unsubstituted aromatic hydrocarbon group optionally having a condensed ring, which is represented by the formula (4):

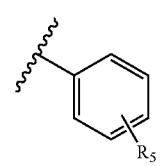

wherein R₂ represents a substituted or unsubstituted thiophenyl group, wherein, in the formula (4), R₅ represents 1 to 5 identical or different substituents on a benzene ring, each of which independently represents a hydrogen atom, a halogen atom, a hydroxyl group, a nitro group, a cyano group, a carboxy group, a lower alkoxy group, a lower alkoxyalkyl group, a lower alkoxycarbonyl group, a lower acyl group, a lower acyloxy group, a lower acyloxyalkyl group, a carbamoyl group, a sulfamoyl group, a trifluoromethyl group, a substituted or unsubstituted allyl group, a substituted or unsubstituted heteroallyl group, a substituted or unsubstituted phenoxy group, a substituted or unsubstituted amino group, a substituted or unsubstituted lower alkyl group, a substituted or unsubstituted lower alkenyl group, a substituted or unsubstituted aromatic hydrocarbon group, or a substituted or unsubstituted aromatic heterocyclic group;

wherein, in the formula (4), if there are a plurality of substituents, a ring may be formed by such a plurality of substituents;

wherein the disease is Alzheimer's disease, and wherein the subject is a subject in need of treatment of Alzheimer's disease.

16. The method according to claim 15, wherein the compound represented by the general formula (1) is selected from the group consisting of:

4-((4-methoxyphenyl)methylene)-2-(2-thienyl)-5(4H)-oxazolone, methyl 4-((5-oxo-2-(2-thienyl)oxazol-4(5H)-ylidene)methyl)benzoate, 4-((4-methoxy-3-nitrophenyl)methylene)-2-(2-thienyl)-5(4H)-oxazolone, 4-((6-chloro-1,3-benzodioxol-5-yl)methylene)-2-(2-thienyl)-5(4H)-oxazolone, 4-((3-chloro-4-nitrophenyl)methylene)-2-(2-thienyl)-5(4H)-oxazolone, 4-((3-bromo-4-nitrophenyl)methylene)-2-(2-thienyl)-5(4H)-oxazolone, and 4-((8-chloro-2,3-dihydro-1,4-benzodioxin-6-yl)methylene)-2-(2-thienyl)-5(4H)-oxazolone.

17. A method for treating a disease, with the pathological condition of which the activation of casein kinase 1δ or casein kinase 1ε is associated, comprising:

administering to a subject at least one of an oxazolone derivative represented by the following general formula (1), a salt thereof, a solvate thereof, or a hydrate thereof:

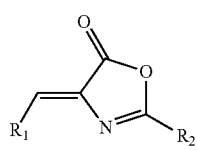

(1)

wherein R₁ represents a substituted or unsubstituted 5-membered heterocyclic group optionally having a condensed ring, which is represented by the formula (3a) or (3b),

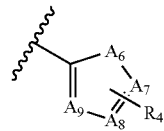

(3a)

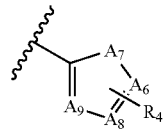

(3b)

wherein R₂ represents a substituted or unsubstituted thiophenyl group, wherein in the formula (3a) or (3b), A₆ represents an oxygen atom, a sulfur atom or a nitrogen atom;

wherein, in the formula (3a) or (3b), A₇, A₈ and A₉ each represent a carbon atom or a nitrogen atom;

wherein, in the formula (3a) or (3b), R₄ represents 1 to 4 identical or different substituents on A₆ to A₉, each of which independently represents a hydrogen atom, a halogen atom, a hydroxyl group, a nitro group, a cyano group, a carboxy group, a lower alkoxy group, a lower alkoxyalkyl group, a lower alkoxycarbonyl group, a lower acyl group, a lower acyloxy group, a lower acyloxyalkyl group, a carbamoyl group, a sulfamoyl group, a trifluoromethyl group, a substituted or unsubstituted allyl group, a substituted or unsubstituted heteroallyl group, a substituted or unsubstituted phenoxy group, a substituted or unsubstituted amino group, a substituted or unsubstituted lower alkyl group, a substituted or unsubstituted lower alkenyl group, a substituted or unsubstituted aromatic hydrocarbon group, or a substituted or unsubstituted aromatic heterocyclic group;

wherein, in the formula (3a) or (3b), if there are a plurality of substituents, a ring may be formed by such a plurality of substituents;

wherein the disease is Alzheimer's disease, and wherein the subject is a subject in need of treatment of Alzheimer's disease.

18. The method according to claim 17, wherein the compound represented by the general formula (1) is selected from the group consisting of:

4-((1-methyl-1H-pyrazol-4-yl)methylene)-2-(2-thienyl)-5(4H)-oxazolone, 4-((1-methyl-1H-imidazol-4-yl)methylene)-2-(2-thienyl)-5(4H)-oxazolone, 4-((5-acetyloxymethyl-2-furanyl)methylene)-2-(2-thienyl)-5(4H)-oxazolone, 4-((5-methoxymethyl-2-furanyl)methylene)-2-(2-thienyl)-5(4H)-oxazolone, 4-((4-oxazolyl)methylene)-2-(2-thienyl)-5(4H)-oxazolone, 4-((1,2,3-thiadiazol-4-yl)methylene)-2-(2-thienyl)-5(4H)-oxazolone, 4-((1,5-dimethyl-1H-pyrazol-4-yl)methylene)-2-(2-thienyl)-5(4H)-oxazolone, and 4-((1,3-dimethyl-1H-pyrazol-4-yl)methylene)-2-(2-thienyl)-5(4H)-oxazolone.

19. The method according to claim 12, wherein the compound represented by the general formula (1) is 4-((6-methoxy-3-pyridinyl)methylene)-2-(2-thienyl)-5(4H)-oxazolone.

20. The method according to claim 1, wherein the circadian rhythm sleep disorder is insomnia, jet lag syndrome, shift work sleep disorder, advanced sleep phase syndrome or delayed sleep phase syndrome.

* * * * *